(12) United States Patent
Julian et al.

(10) Patent No.: US 11,986,257 B2
(45) Date of Patent: May 21, 2024

(54) MEDICAL INSTRUMENT WITH ARTICULABLE SEGMENT

(71) Applicant: Auris Health, Inc., Redwood City, CA (US)

(72) Inventors: Christopher Allen Julian, Los Gatos, CA (US); Thomas R. Jenkins, Alameda, CA (US)

(73) Assignee: Auris Health, Inc., Redwood City, CA (US)

( * ) Notice: Subject to any disclaimer, the term of this patent is extended or adjusted under 35 U.S.C. 154(b) by 835 days.

(21) Appl. No.: 16/727,760

(22) Filed: Dec. 26, 2019

(65) Prior Publication Data
US 2020/0205908 A1 Jul. 2, 2020

Related U.S. Application Data

(60) Provisional application No. 62/868,801, filed on Jun. 28, 2019, provisional application No. 62/786,133, filed on Dec. 28, 2018.

(51) Int. Cl.
*A61B 34/30* (2016.01)
*A61B 1/05* (2006.01)
(Continued)

(52) U.S. Cl.
CPC .............. *A61B 34/30* (2016.02); *A61B 1/05* (2013.01); *A61B 17/00234* (2013.01);
(Continued)

(58) Field of Classification Search
CPC ..... A61B 34/30; A61B 1/05; A61B 17/00234; A61B 2017/00323; A61B 2017/00336;
(Continued)

(56) References Cited

U.S. PATENT DOCUMENTS 3,060,972 A * 10/1962 Sheldon ............... A61B 1/0055
138/120
3,572,325 A 3/1971 Bazell et al.
(Continued)

FOREIGN PATENT DOCUMENTS

CN 1846181 10/2006
CN 1857877 11/2006
(Continued)

OTHER PUBLICATIONS

EP Search Report for Appl. No. 19902914.1, dated Jun. 29, 2022, 12 pages.
(Continued)

*Primary Examiner* — Anh Tuan T Nguyen
*Assistant Examiner* — Shankar Raj Ghimire
(74) *Attorney, Agent, or Firm* — Chang & Hale LLP

(57) ABSTRACT

Certain aspects relate to systems and techniques for a medical device. The medical device can include an elongated shaft having a proximal end, a distal end, and a bendable section between the proximal end and the distal end. The medical device can include a tip assembly at the distal end of the elongated shaft. The tip assembly include a control member and a distal tip component attached to the control member. At least one cable can extend through the elongated shaft and be anchored to the control member. The at least one cable can be configured to bend the bendable section based on a force applied thereto. At least one electronic component can be embedded in the distal tip component.

7 Claims, 30 Drawing Sheets

(51) Int. Cl.
  *A61B 17/00* (2006.01)
  *A61B 1/06* (2006.01)
  *A61B 17/22* (2006.01)
  *A61B 18/26* (2006.01)
  *A61B 34/00* (2016.01)
  *A61B 34/37* (2016.01)
  *A61B 90/00* (2016.01)
  *A61M 25/01* (2006.01)

(52) U.S. Cl.
  CPC ... *A61B 1/0661* (2013.01); *A61B 2017/00199* (2013.01); *A61B 2017/00323* (2013.01); *A61B 2017/00336* (2013.01); *A61B 17/22004* (2013.01); *A61B 18/26* (2013.01); *A61B 2034/301* (2016.02); *A61B 34/37* (2016.02); *A61B 2034/743* (2016.02); *A61B 2090/3762* (2016.02); *A61B 2090/3764* (2016.02); *A61B 2217/005* (2013.01); *A61B 2217/007* (2013.01); *A61M 25/0127* (2013.01)

(58) Field of Classification Search
  CPC ...... A61B 2034/301; A61B 2090/3764; A61B 2034/306; A61B 1/00149; A61B 1/0057; A61B 1/0055; A61B 2017/00314; A61B 2017/00477; A61M 25/0127
  See application file for complete search history.

(56) References Cited

U.S. PATENT DOCUMENTS

| | | | |
|---|---|---|---|
| 3,913,565 A | 10/1975 | Kawahara | |
| 4,294,234 A | 10/1981 | Matsuo | |
| 4,392,485 A | 7/1983 | Hiltebrandt | |
| 4,607,619 A | 8/1986 | Seike et al. | |
| 4,690,175 A | 9/1987 | Ouchi et al. | |
| 4,706,656 A | 11/1987 | Kubota | |
| 4,741,326 A | 5/1988 | Sidall et al. | |
| 4,745,908 A | 5/1988 | Wardle | |
| 4,748,969 A | 6/1988 | Wardle | |
| 4,750,475 A | 6/1988 | Yoshihashi | |
| 4,771,766 A | 9/1988 | Aoshiro | |
| 4,834,069 A * | 5/1989 | Umeda | A61B 34/71 138/120 |
| 4,846,791 A | 7/1989 | Hattler et al. | |
| 4,869,238 A | 9/1989 | Opie et al. | |
| 4,906,496 A | 3/1990 | Hosono et al. | |
| 4,907,168 A | 3/1990 | Boggs | |
| 4,967,732 A | 11/1990 | Inoue | |
| 5,005,558 A * | 4/1991 | Aomori | A61B 1/0055 600/149 |
| 5,050,585 A | 9/1991 | Takahashi | |
| 5,083,549 A | 1/1992 | Cho et al. | |
| 5,106,387 A | 4/1992 | Kittrell et al. | |
| 5,108,800 A | 4/1992 | Koo | |
| 5,125,909 A | 6/1992 | Heimberger | |
| 5,168,864 A | 12/1992 | Shockey | |
| 5,178,129 A * | 1/1993 | Chikama | A61B 1/0055 600/920 |
| 5,217,002 A | 6/1993 | Katsurada | |
| 5,251,611 A | 10/1993 | Zehel | |
| 5,257,617 A | 11/1993 | Takahashi | |
| 5,261,391 A | 11/1993 | Inoue | |
| 5,271,381 A * | 12/1993 | Ailinger | A61B 1/0055 600/128 |
| 5,287,861 A | 2/1994 | Wilk | |
| 5,313,934 A | 5/1994 | Wiita et al. | |
| 5,386,818 A | 2/1995 | Schneebaum | |
| 5,448,988 A | 9/1995 | Watanabe | |
| 5,448,989 A * | 9/1995 | Heckele | A61B 1/0052 600/149 |
| 5,454,827 A * | 10/1995 | Aust | A61B 1/0052 606/174 |
| 5,478,330 A | 12/1995 | Imran et al. | |
| 5,479,930 A * | 1/1996 | Gruner | A61B 34/71 600/463 |
| 5,482,029 A | 1/1996 | Sekiguchi | |
| 5,489,270 A | 2/1996 | van Erp | |
| 5,507,725 A | 4/1996 | Savage et al. | |
| 5,533,985 A | 7/1996 | Wang | |
| 5,580,200 A | 12/1996 | Fullerton | |
| 5,624,453 A * | 4/1997 | Ahmed | A61B 17/12013 606/139 |
| 5,681,296 A | 10/1997 | Ishida | |
| 5,704,534 A | 1/1998 | Huitema et al. | |
| 5,720,775 A | 2/1998 | Lamard | |
| 5,741,429 A | 4/1998 | Donadio, III | |
| 5,749,889 A | 5/1998 | Bacich et al. | |
| 5,755,731 A * | 5/1998 | Grinberg | A61B 17/32002 606/180 |
| 5,873,817 A * | 2/1999 | Kokish | A61B 1/0058 600/151 |
| 5,876,325 A | 3/1999 | Mizuno et al. | |
| 5,879,287 A | 3/1999 | Yoshihashi | |
| 5,882,347 A | 3/1999 | Mouris-Laan | |
| 5,888,191 A | 3/1999 | Akiba | |
| 5,910,129 A | 6/1999 | Koblish et al. | |
| 5,938,586 A | 8/1999 | Wilk | |
| 5,938,587 A | 8/1999 | Taylor et al. | |
| 6,012,494 A | 1/2000 | Balazs | |
| 6,143,013 A | 11/2000 | Samson et al. | |
| 6,157,853 A | 12/2000 | Blume et al. | |
| 6,174,280 B1 | 1/2001 | Oneda | |
| 6,197,015 B1 | 3/2001 | Wilson | |
| 6,198,974 B1 | 3/2001 | Webster, Jr. | |
| 6,234,958 B1 | 5/2001 | Snoke et al. | |
| 6,270,453 B1 * | 8/2001 | Sakai | A61B 1/008 600/141 |
| 6,315,715 B1 | 11/2001 | Taylor et al. | |
| 6,404,497 B1 | 6/2002 | Backman | |
| 6,436,107 B1 | 8/2002 | Wang et al. | |
| 6,464,632 B1 | 10/2002 | Taylor | |
| 6,485,411 B1 | 11/2002 | Konstorum | |
| 6,491,626 B1 | 12/2002 | Stone et al. | |
| 6,537,205 B1 | 3/2003 | Smith | |
| 6,554,793 B1 | 4/2003 | Pauker et al. | |
| 6,716,178 B1 | 4/2004 | Kilpatrick et al. | |
| 6,746,422 B1 | 6/2004 | Noriega | |
| 6,749,560 B1 | 6/2004 | Konstorum | |
| 6,790,173 B2 | 9/2004 | Saadat | |
| 6,817,974 B2 * | 11/2004 | Cooper | A61B 17/00234 606/205 |
| 6,827,710 B1 | 12/2004 | Mooney et al. | |
| 6,827,712 B2 | 12/2004 | Tovey et al. | |
| 6,837,846 B2 | 1/2005 | Jaffe | |
| 6,908,428 B2 | 6/2005 | Aizenfeld | |
| 6,921,362 B2 | 7/2005 | Ouchi | |
| 6,958,035 B2 | 10/2005 | Friedman et al. | |
| 7,008,401 B2 | 3/2006 | Thompson et al. | |
| 7,130,700 B2 * | 10/2006 | Gardeski | A61M 25/0021 607/116 |
| 7,594,903 B2 | 9/2009 | Webler et al. | |
| 7,645,230 B2 | 1/2010 | Mikkaichi | |
| 7,645,231 B2 | 1/2010 | Akiba | |
| 7,789,827 B2 | 9/2010 | Landry | |
| 7,930,065 B2 | 4/2011 | Larkin et al. | |
| 8,046,049 B2 | 10/2011 | Govari et al. | |
| 8,052,636 B2 | 11/2011 | Moll et al. | |
| 8,246,536 B2 | 8/2012 | Ochi | |
| 8,376,865 B2 * | 2/2013 | Forster | A61M 25/0043 464/78 |
| 8,444,637 B2 * | 5/2013 | Podmore | A61B 17/00234 604/95.04 |
| 8,460,236 B2 | 6/2013 | Roelle et al. | |
| 8,498,691 B2 | 7/2013 | Moll et al. | |
| 8,515,215 B2 | 8/2013 | Younge et al. | |
| 8,562,518 B2 * | 10/2013 | Kitagawa | A61B 1/008 403/54 |
| 8,622,894 B2 * | 1/2014 | Banik | A61B 1/0016 600/141 |
| 8,652,030 B2 | 2/2014 | Matsuura et al. | |
| 8,686,747 B2 | 4/2014 | Berner | |

(56) References Cited

U.S. PATENT DOCUMENTS

| | | | |
|---|---|---|---|
| 8,758,231 B2 * | 6/2014 | Bunch | A61B 1/0055 600/141 |
| 8,827,947 B2 | 9/2014 | Bosman et al. | |
| 8,939,899 B2 * | 1/2015 | Kitagawa | A61B 1/0055 600/141 |
| 9,186,046 B2 | 11/2015 | Ramamurthy et al. | |
| 9,314,953 B2 | 4/2016 | Lauer | |
| 9,427,551 B2 | 8/2016 | Leeflang et al. | |
| 9,504,604 B2 | 11/2016 | Alvarez | |
| 9,561,083 B2 | 2/2017 | Yu et al. | |
| 9,591,990 B2 | 3/2017 | Chen et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,918,659 B2 * | 3/2018 | Chopra | A61B 5/064 |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,130,427 B2 | 11/2018 | Tanner et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,363,103 B2 | 7/2019 | Alvarez et al. | |
| 10,376,672 B2 | 8/2019 | Yu | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,463,439 B2 | 11/2019 | Joseph et al. | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,500,001 B2 | 12/2019 | Yu et al. | |
| 10,517,692 B2 | 12/2019 | Eyre et al. | |
| 10,524,866 B2 | 1/2020 | Srinivasan | |
| 10,539,478 B2 | 1/2020 | Lin | |
| 10,543,048 B2 | 1/2020 | Noonan et al. | |
| 10,555,778 B2 | 2/2020 | Ummalaneni et al. | |
| 10,555,780 B2 | 2/2020 | Tanner et al. | |
| 10,765,487 B2 | 9/2020 | Ho | |
| 11,419,692 B2 * | 8/2022 | Kim | A61B 34/71 |
| 2001/0004676 A1 | 6/2001 | Ouchi | |
| 2003/0036748 A1 | 2/2003 | Cooper et al. | |
| 2003/0130564 A1 | 7/2003 | Martone et al. | |
| 2003/0158545 A1 | 8/2003 | Hovda et al. | |
| 2003/0163199 A1 | 8/2003 | Chu et al. | |
| 2003/0195664 A1 | 10/2003 | Nowlin et al. | |
| 2004/0015122 A1 | 1/2004 | Zhang et al. | |
| 2004/0054322 A1 | 3/2004 | Vargas | |
| 2004/0072066 A1 | 4/2004 | Cho et al. | |
| 2004/0138525 A1 | 7/2004 | Saadat et al. | |
| 2004/0193013 A1 | 9/2004 | Isakawa et al. | |
| 2004/0236316 A1 * | 11/2004 | Danitz | A61B 34/70 606/1 |
| 2004/0249246 A1 | 12/2004 | Campos | |
| 2005/0004515 A1 | 1/2005 | Hart et al. | |
| 2005/0125005 A1 | 6/2005 | Fujikura | |
| 2005/0131279 A1 * | 6/2005 | Boulais | A61B 1/00071 600/141 |
| 2005/0154262 A1 | 7/2005 | Banik et al. | |
| 2005/0159646 A1 | 7/2005 | Nordstrom et al. | |
| 2005/0165366 A1 | 7/2005 | Brustad | |
| 2005/0182298 A1 * | 8/2005 | Ikeda | A61B 34/70 600/104 |
| 2005/0222581 A1 | 10/2005 | Fischer et al. | |
| 2005/0234293 A1 | 10/2005 | Yamamoto | |
| 2005/0256452 A1 | 11/2005 | DeMarchi | |
| 2005/0272975 A1 | 12/2005 | McWeeney et al. | |
| 2005/0272978 A1 * | 12/2005 | Brunnen | A61B 1/008 600/142 |
| 2005/0273085 A1 | 12/2005 | Hinman et al. | |
| 2005/0288549 A1 | 12/2005 | Mathis | |
| 2006/0041188 A1 | 2/2006 | Dirusso et al. | |
| 2006/0111692 A1 | 5/2006 | Hlavka et al. | |
| 2006/0178556 A1 * | 8/2006 | Hasser | A61B 34/35 600/102 |
| 2006/0199999 A1 * | 9/2006 | Ikeda | A61B 1/00149 600/141 |
| 2006/0241368 A1 | 10/2006 | Fichtinger et al. | |
| 2006/0264708 A1 | 11/2006 | Horne | |
| 2006/0276827 A1 | 12/2006 | Mitelberg et al. | |
| 2006/0287769 A1 | 12/2006 | Yanagita et al. | |
| 2007/0060879 A1 | 3/2007 | Weitzner et al. | |
| 2007/0112355 A1 | 5/2007 | Salahieh | |
| 2007/0135733 A1 | 6/2007 | Soukup et al. | |
| 2007/0135763 A1 | 6/2007 | Musbach et al. | |
| 2007/0135803 A1 | 6/2007 | Belson | |
| 2007/0156019 A1 | 7/2007 | Larkin et al. | |
| 2007/0270645 A1 | 11/2007 | Ikeda | |
| 2007/0270679 A1 | 11/2007 | Nguyen et al. | |
| 2007/0282167 A1 | 12/2007 | Barenboym et al. | |
| 2007/0287886 A1 | 12/2007 | Saadat | |
| 2008/0039255 A1 | 2/2008 | Jinno et al. | |
| 2008/0051629 A1 | 2/2008 | Sugiyama et al. | |
| 2008/0065103 A1 | 3/2008 | Cooper et al. | |
| 2008/0097293 A1 | 4/2008 | Chin et al. | |
| 2008/0108869 A1 | 5/2008 | Sanders et al. | |
| 2008/0139887 A1 | 6/2008 | Fitpatrick | |
| 2008/0146874 A1 | 6/2008 | Miller | |
| 2008/0147089 A1 | 6/2008 | Loh | |
| 2008/0177285 A1 | 7/2008 | Brock et al. | |
| 2008/0208001 A1 | 8/2008 | Hadani | |
| 2008/0212082 A1 | 9/2008 | Froggatt et al. | |
| 2008/0218770 A1 | 9/2008 | Moll et al. | |
| 2009/0099420 A1 | 4/2009 | Woodley et al. | |
| 2009/0163851 A1 | 6/2009 | Holloway | |
| 2009/0247880 A1 | 10/2009 | Naruse et al. | |
| 2009/0254083 A1 | 10/2009 | Wallace et al. | |
| 2009/0299344 A1 | 12/2009 | Lee et al. | |
| 2009/0306587 A1 | 12/2009 | Milijasevic et al. | |
| 2010/0030023 A1 | 2/2010 | Yoshie | |
| 2010/0057101 A1 * | 3/2010 | Karpiel | A61B 17/0643 606/140 |
| 2010/0073150 A1 | 3/2010 | Olson et al. | |
| 2010/0114115 A1 | 5/2010 | Schlesinger et al. | |
| 2010/0130823 A1 | 5/2010 | Ando | |
| 2010/0168918 A1 | 7/2010 | Zhao | |
| 2010/0217184 A1 | 8/2010 | Koblish et al. | |
| 2010/0228284 A1 * | 9/2010 | Cooper | A61B 34/30 606/206 |
| 2010/0249497 A1 | 9/2010 | Peine et al. | |
| 2010/0249506 A1 | 9/2010 | Prisco et al. | |
| 2011/0009863 A1 | 1/2011 | Stanislaw | |

(56) References Cited

U.S. PATENT DOCUMENTS

| | | |
|---|---|---|
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0245844 A1 | 10/2011 | Jinno et al. |
| 2011/0261183 A1 | 10/2011 | Ma et al. |
| 2011/0306836 A1 | 12/2011 | Ohline et al. |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0204124 A1 | 8/2013 | Duindam |
| 2013/0226151 A1* | 8/2013 | Suehara ............... A61B 1/0055 604/533 |
| 2013/0303892 A1 | 11/2013 | Zhao |
| 2013/0304091 A1 | 11/2013 | Straehnz et al. |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012288 A1 | 1/2014 | Darisse |
| 2014/0046313 A1 | 2/2014 | Pederson et al. |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0276594 A1 | 9/2014 | Tanner et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2015/0031950 A1 | 1/2015 | Drontle et al. |
| 2015/0066002 A1* | 3/2015 | Cooper ............... A61B 34/30 606/1 |
| 2015/0255782 A1 | 9/2015 | Kim et al. |
| 2015/0320501 A1* | 11/2015 | Cooper ............... A61B 17/00 606/130 |
| 2016/0000414 A1 | 1/2016 | Brown |
| 2016/0001038 A1 | 1/2016 | Romo et al. |
| 2016/0007881 A1 | 1/2016 | Wong et al. |
| 2016/0067450 A1* | 3/2016 | Kowshik ........... A61M 25/0147 604/95.04 |
| 2016/0183841 A1 | 6/2016 | Duindam et al. |
| 2016/0227982 A1 | 8/2016 | Takahashi |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0119481 A1 | 5/2017 | Romo et al. |
| 2017/0165011 A1 | 6/2017 | Bovay et al. |
| 2017/0202627 A1 | 7/2017 | Sramek et al. |
| 2017/0209073 A1 | 7/2017 | Sramek et al. |
| 2017/0281218 A1 | 10/2017 | Timm |
| 2017/0281296 A1* | 10/2017 | Cooper ............... A61B 34/72 |
| 2017/0290631 A1 | 10/2017 | Lee et al. |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0046173 A1* | 2/2019 | Cooper ............... A61B 34/72 |
| 2019/0083183 A1 | 3/2019 | Moll et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0307987 A1 | 10/2019 | Yu |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0205908 A1* | 7/2020 | Julian .................. A61B 34/30 |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |

(56) References Cited

U.S. PATENT DOCUMENTS

| | | | |
|---|---|---|---|
| 2020/0268459 A1 | 8/2020 | Noonan et al. | |
| 2020/0268460 A1 | 8/2020 | Tse | |

FOREIGN PATENT DOCUMENTS

| | | |
|---|---|---|
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 1 442 720 | 8/2004 |
| EP | 0 904 796 | 11/2004 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | WO 94/14494 | 7/1994 |
| WO | WO 00/67640 | 11/2000 |
| WO | WO 02/74178 | 9/2002 |
| WO | WO 04/039273 | 5/2004 |
| WO | 2004096015 A2 | 11/2004 |
| WO | 2004103430 A2 | 12/2004 |
| WO | WO 04/105849 | 12/2004 |
| WO | WO 05/032637 | 4/2005 |
| WO | 2004114037 A3 | 9/2005 |
| WO | WO 05/081202 | 9/2005 |
| WO | WO 09/097461 | 6/2007 |
| WO | WO 07/146987 | 12/2007 |
| WO | 2008101228 A2 | 8/2008 |
| WO | WO 08/097540 | 8/2008 |
| WO | WO 09/092059 | 7/2009 |
| WO | WO 10/081187 | 7/2010 |
| WO | 2010093153 A2 | 8/2010 |
| WO | 2010133733 A1 | 11/2010 |
| WO | WO 11/005335 | 1/2011 |
| WO | 2011058530 A1 | 5/2011 |
| WO | 2011100110 A1 | 8/2011 |
| WO | 2013071071 A1 | 5/2013 |
| WO | WO 13/107468 | 7/2013 |
| WO | WO 15/093602 | 12/2013 |
| WO | WO 16/003052 | 1/2016 |

OTHER PUBLICATIONS

International Search Report and Written Opinion in application No. PCT/US2019/068613, dated Apr. 28, 2020.

\* cited by examiner

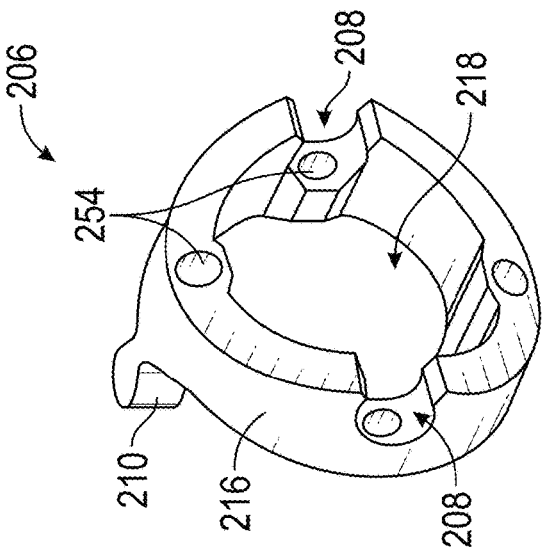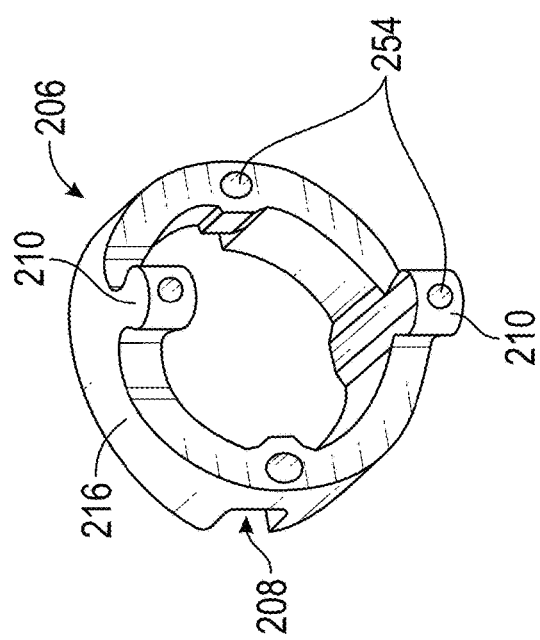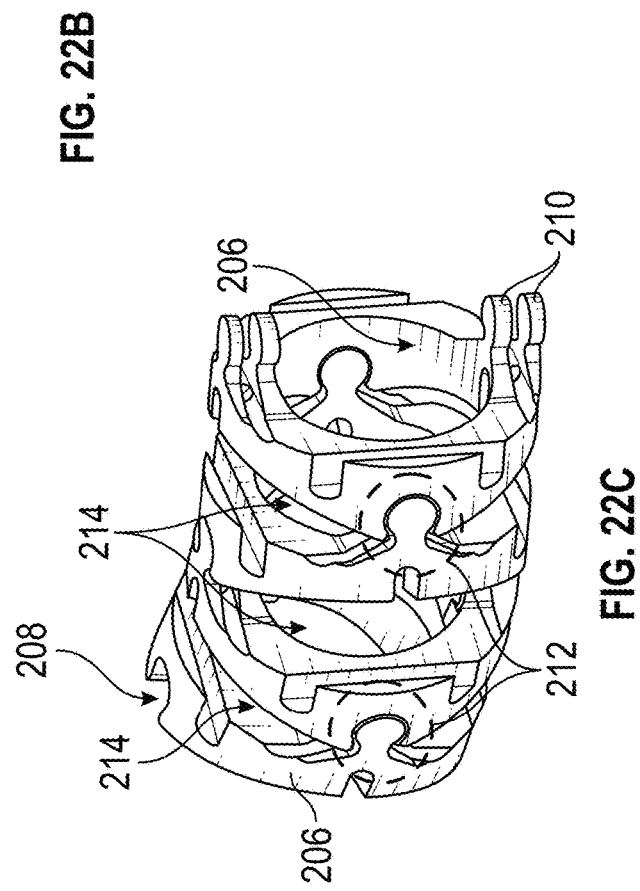
FIG. 22B
FIG. 22C
FIG. 22A

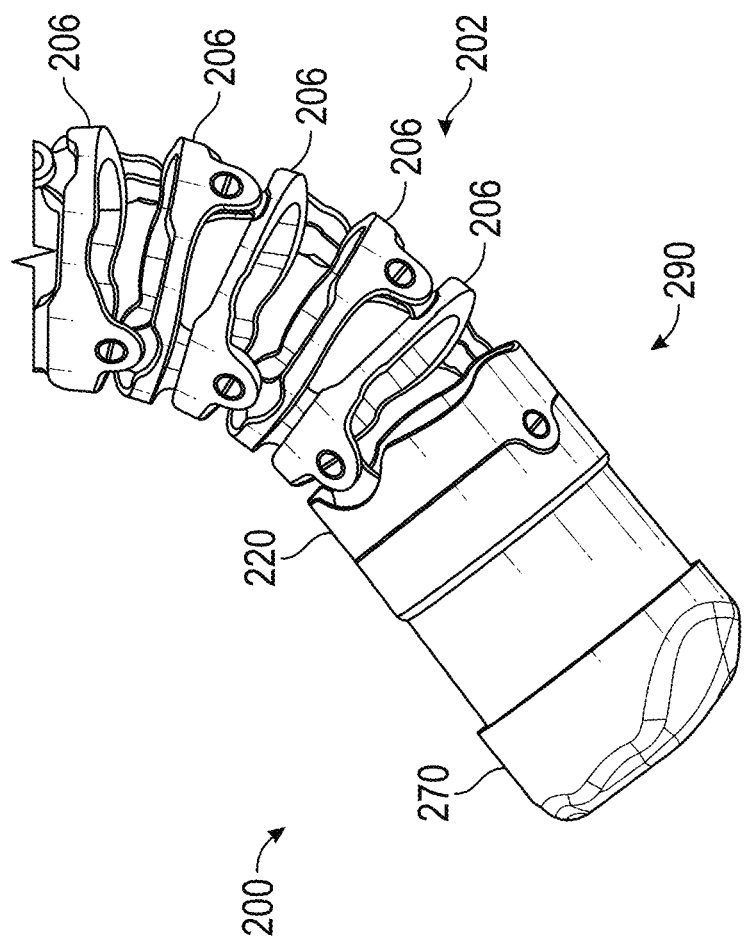

MEDICAL INSTRUMENT WITH ARTICULABLE SEGMENT

CROSS-REFERENCE TO RELATED APPLICATION

This application claims the benefit of U.S. Provisional Application No. 62/786,133, filed Dec. 28, 2018, and U.S. Provisional Application No. 62/868,801, filed Jun. 28, 2019, which are hereby incorporated by reference herein in their entirety.

TECHNICAL FIELD

The systems and methods disclosed herein are directed to medical instruments, and more particularly to medical instruments with bendable sections and tip assemblies.

BACKGROUND

Medical procedures, such as colonoscopy, duodenoscopy, bronchoscopy, ureteroscopy, and the like, may involve using an medical instrument with a bending section to access an internal region of a patient.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 22A and 22B illustrate various views of an articulable segment of the series of articulable segments of FIG. 21B.

FIG. 22C illustrates a series of the articulable segments of FIGS. 22A and 22B.

FIGS. 29A and 29B illustrate various views of a tip assembly for a medical instrument.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
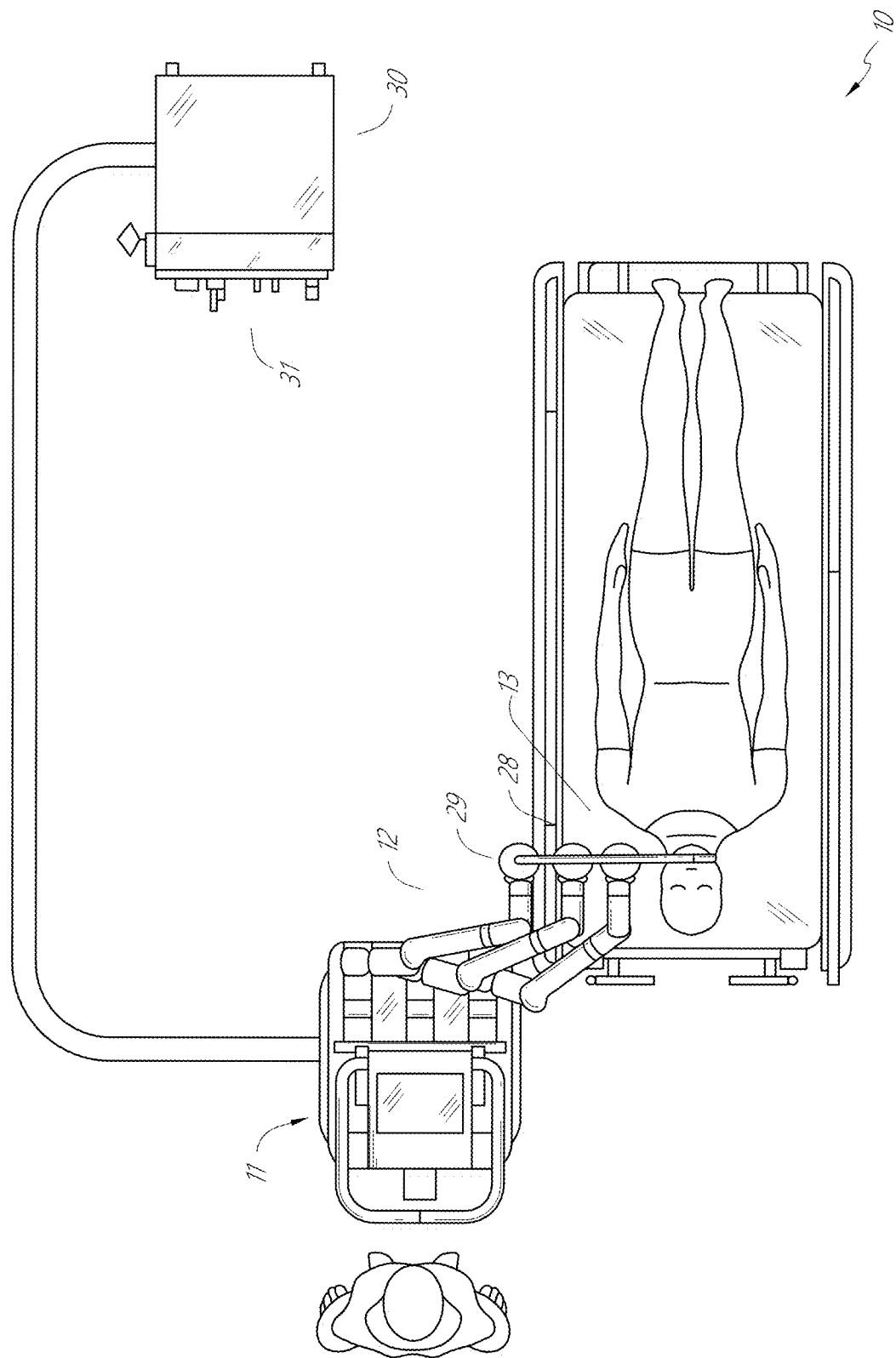
FIG. 1 illustrates an embodiment of a cart-based robotic system arranged for diagnostic and/or therapeutic bronchoscopy procedure(s).
Figure 2:
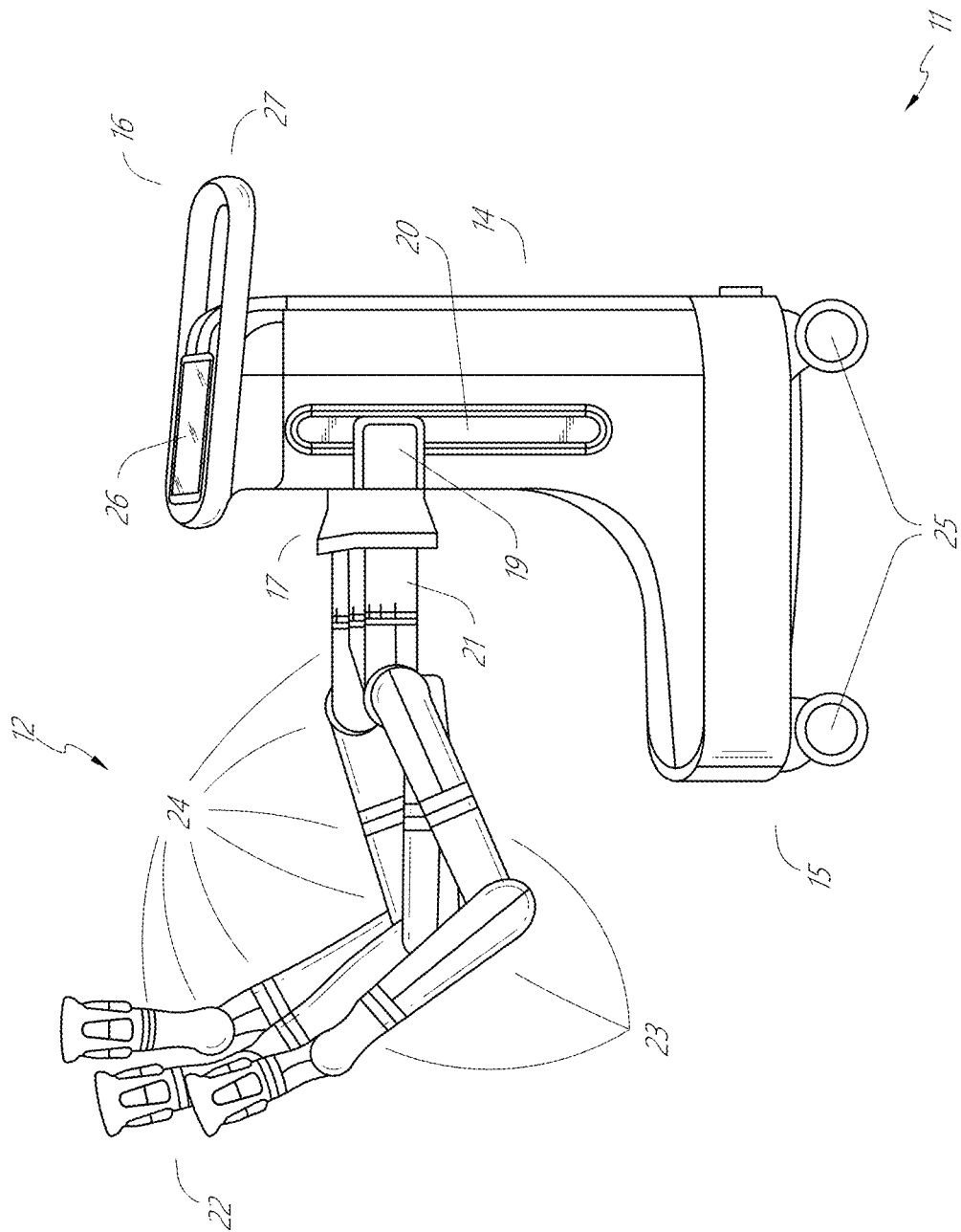
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
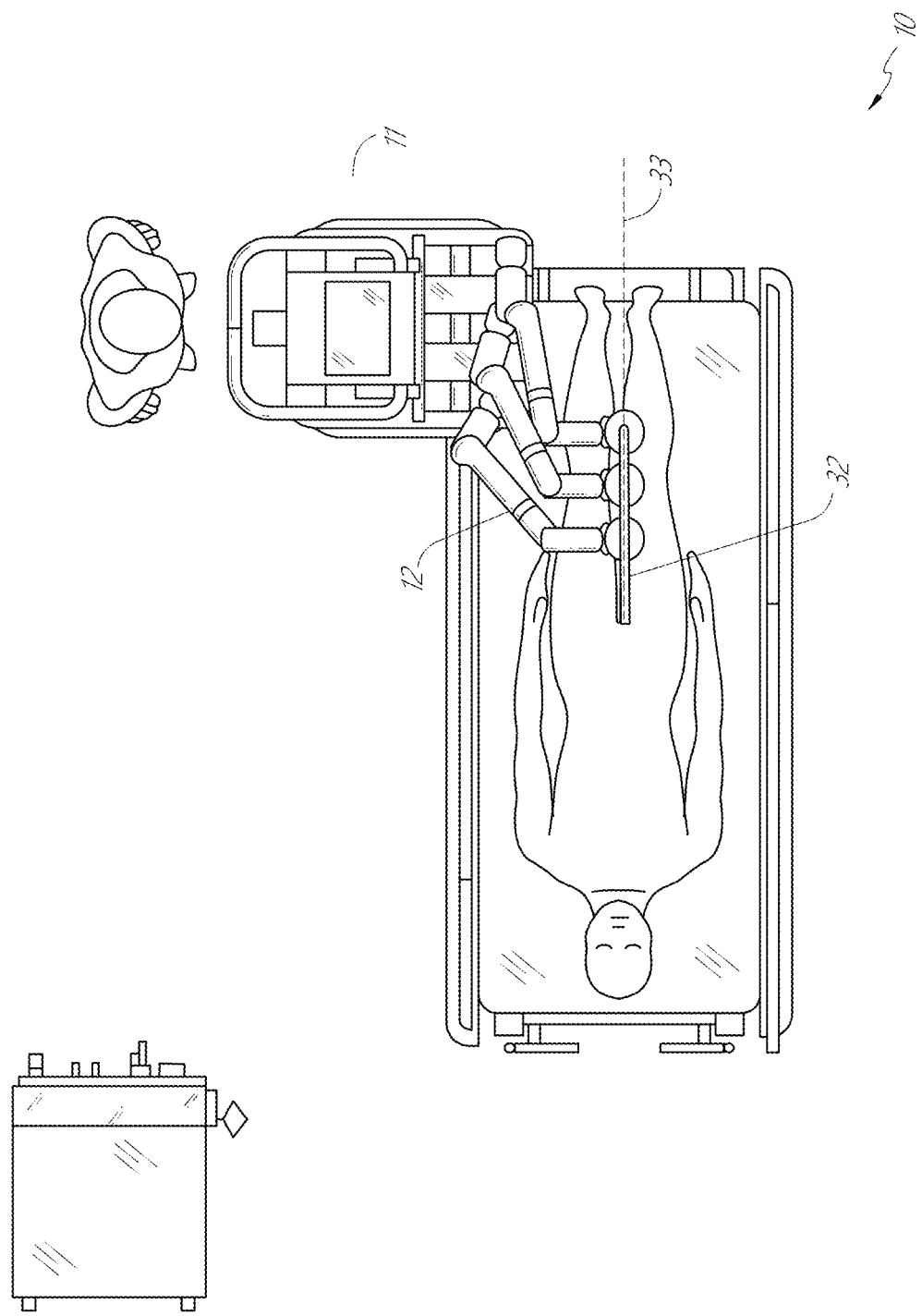
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
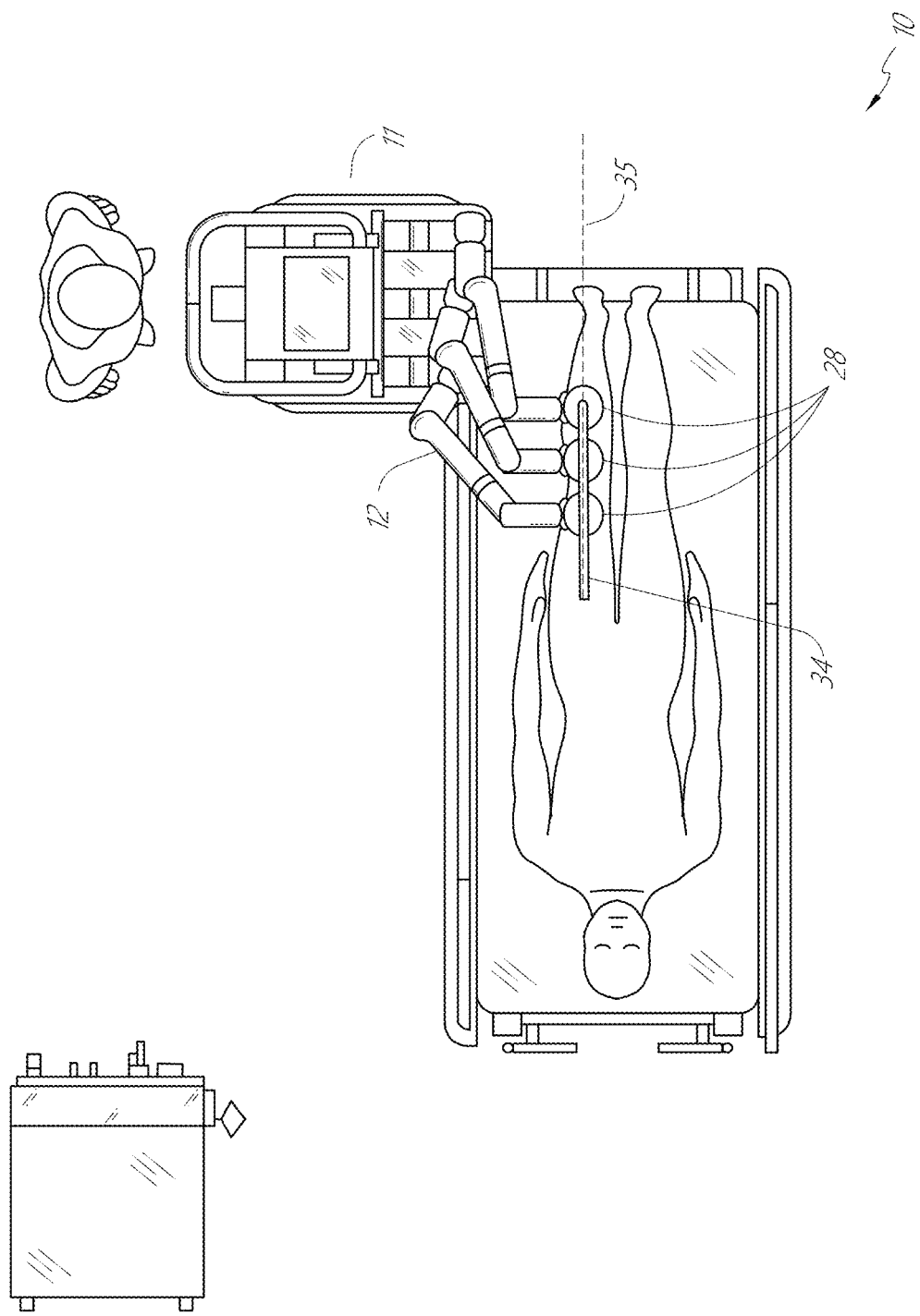
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
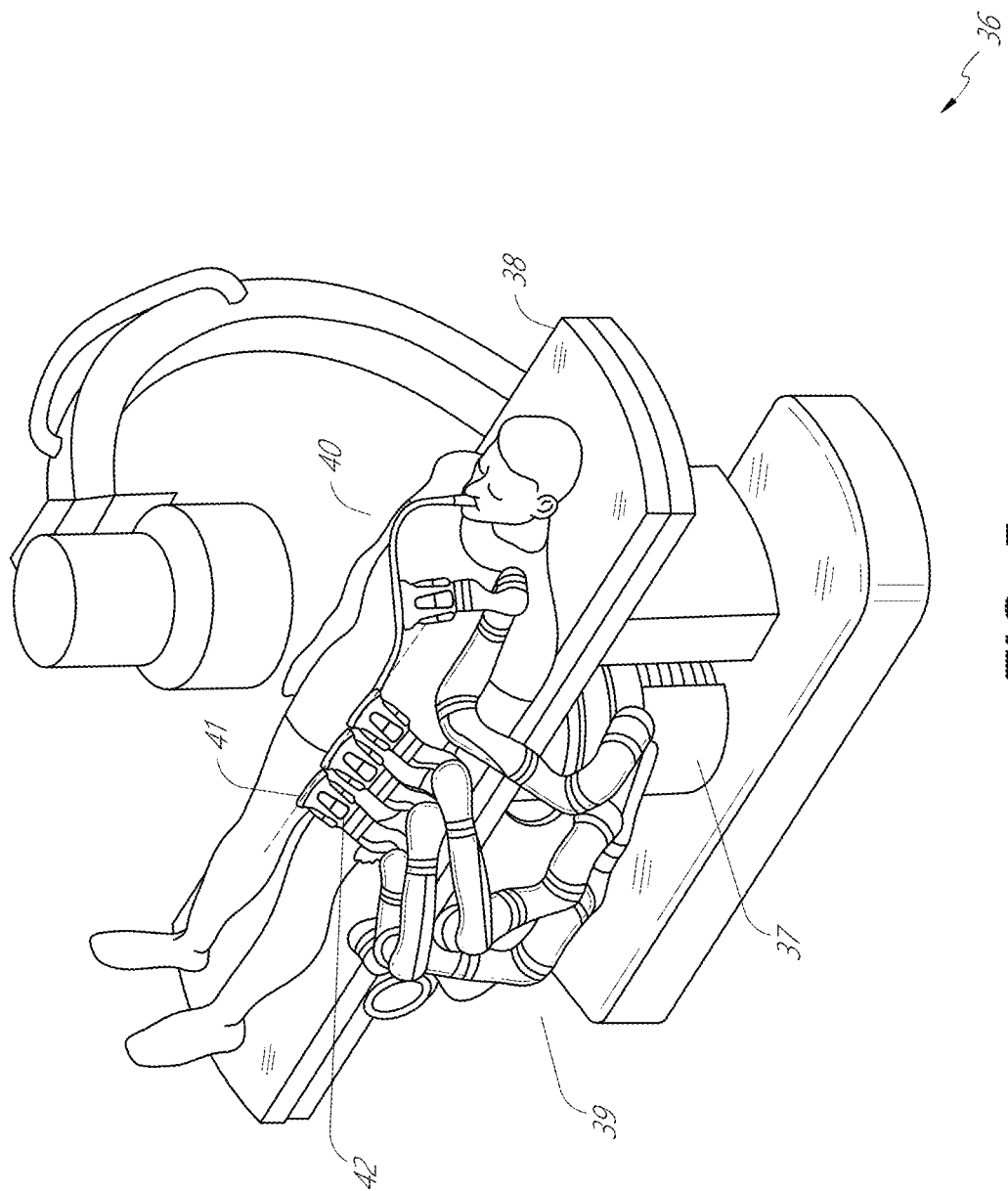
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
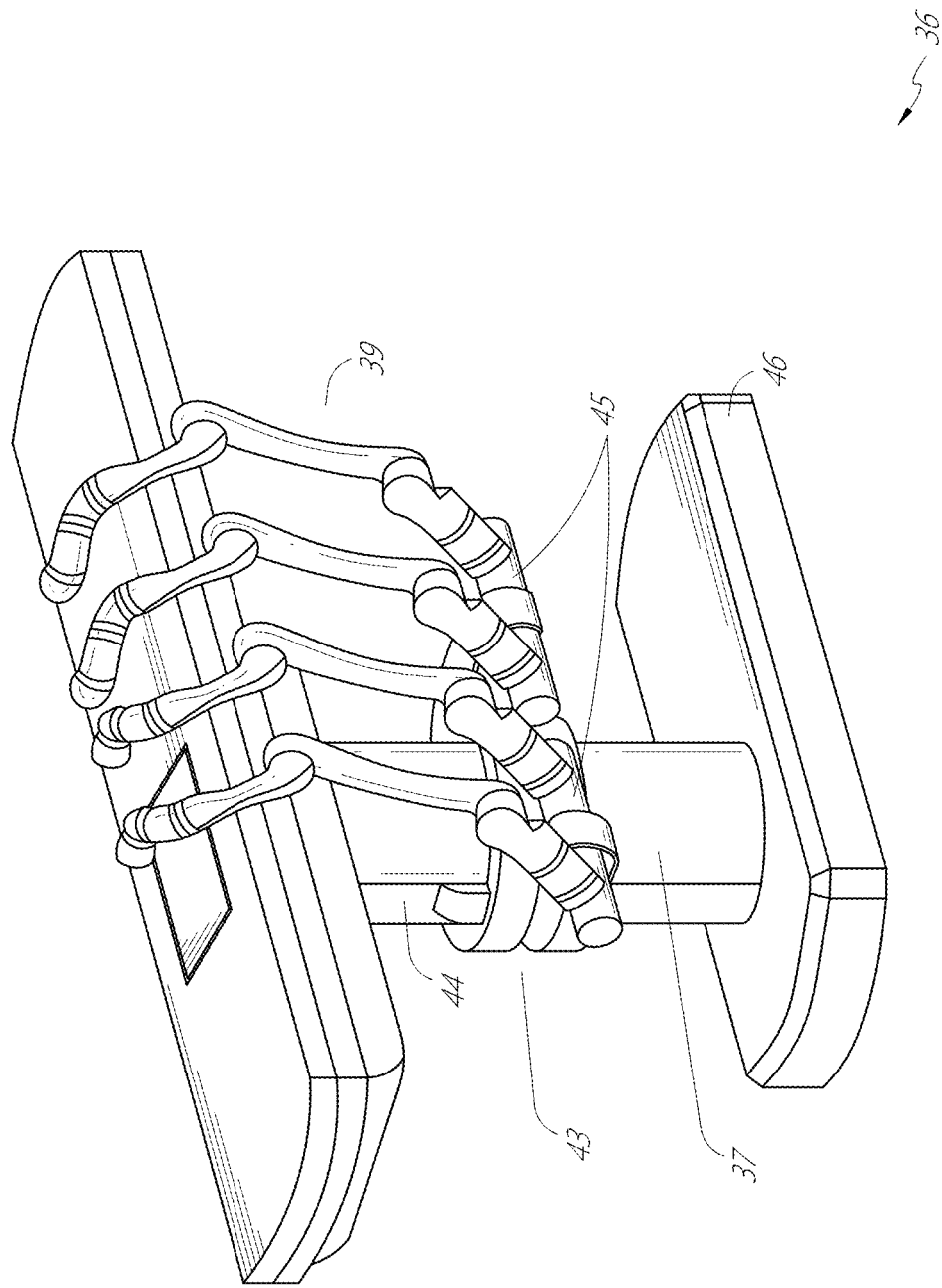
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
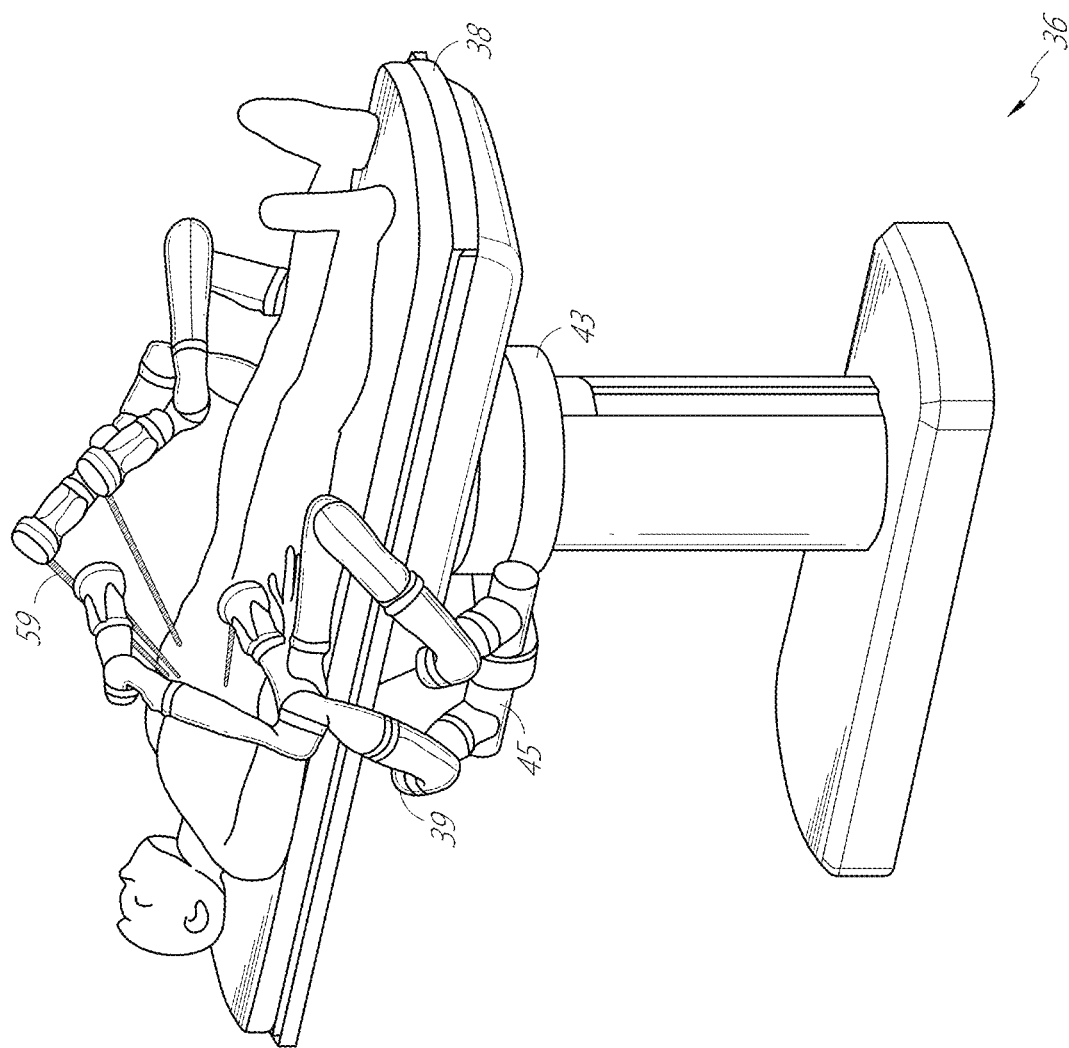
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
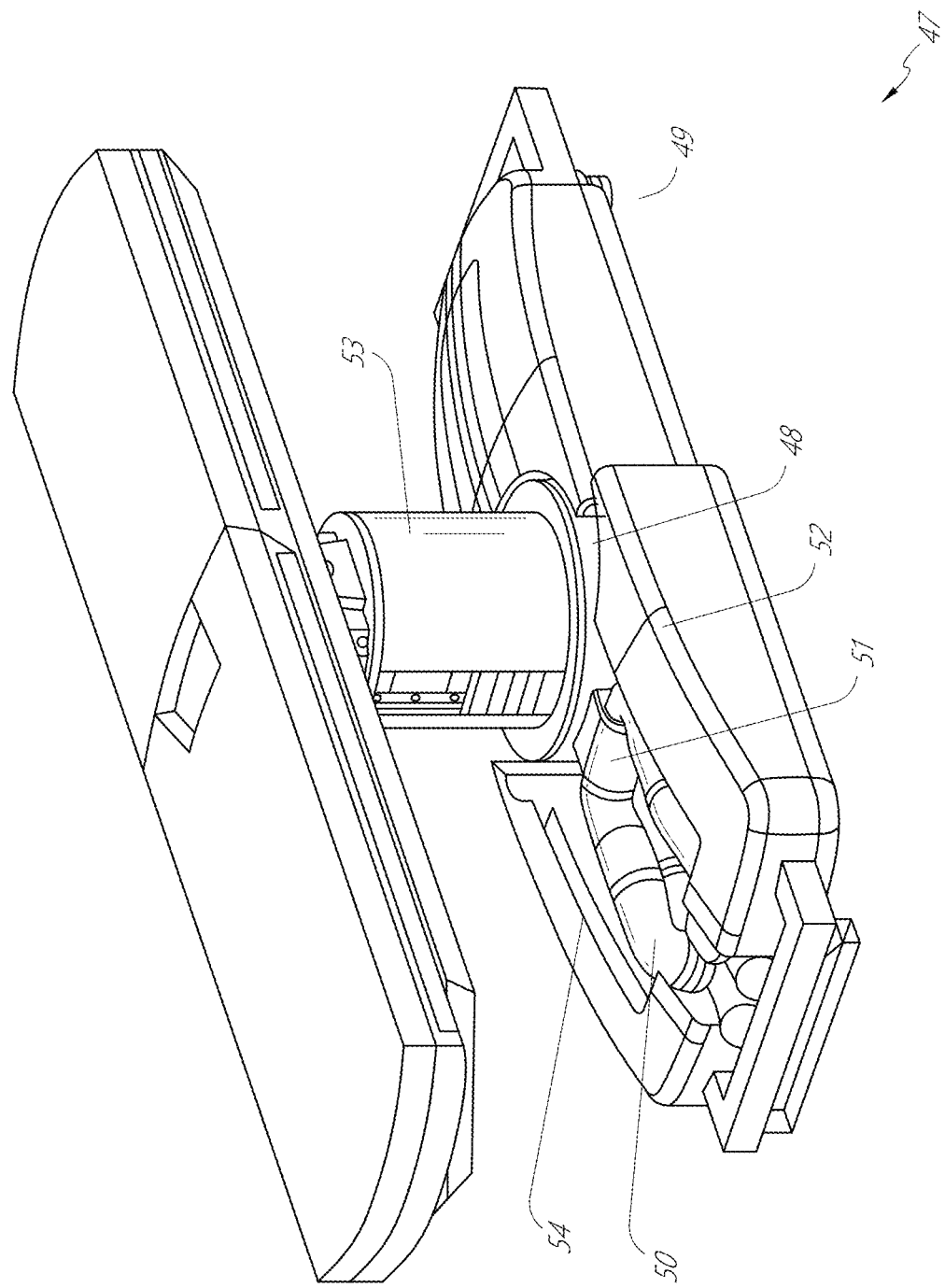
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
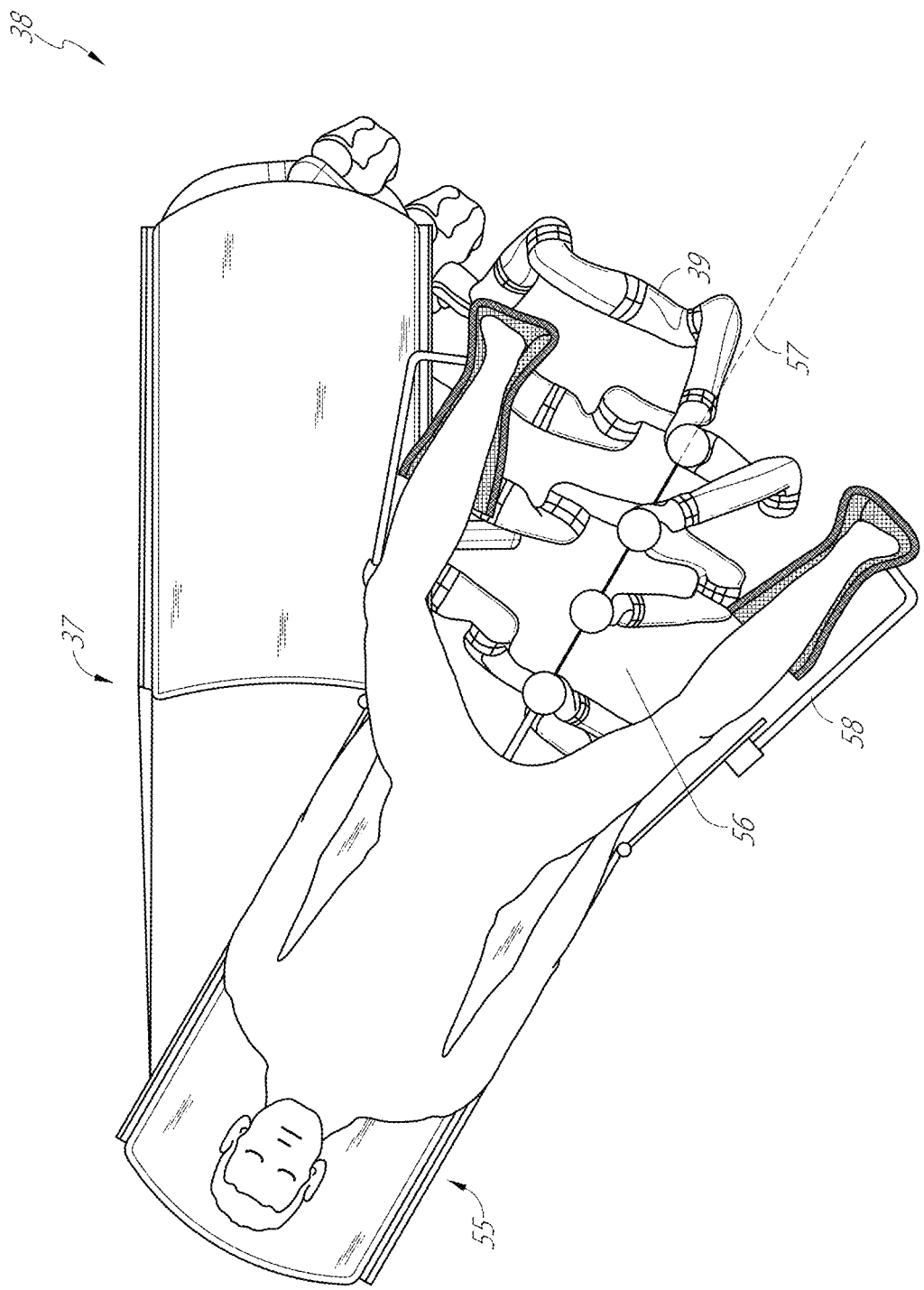
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
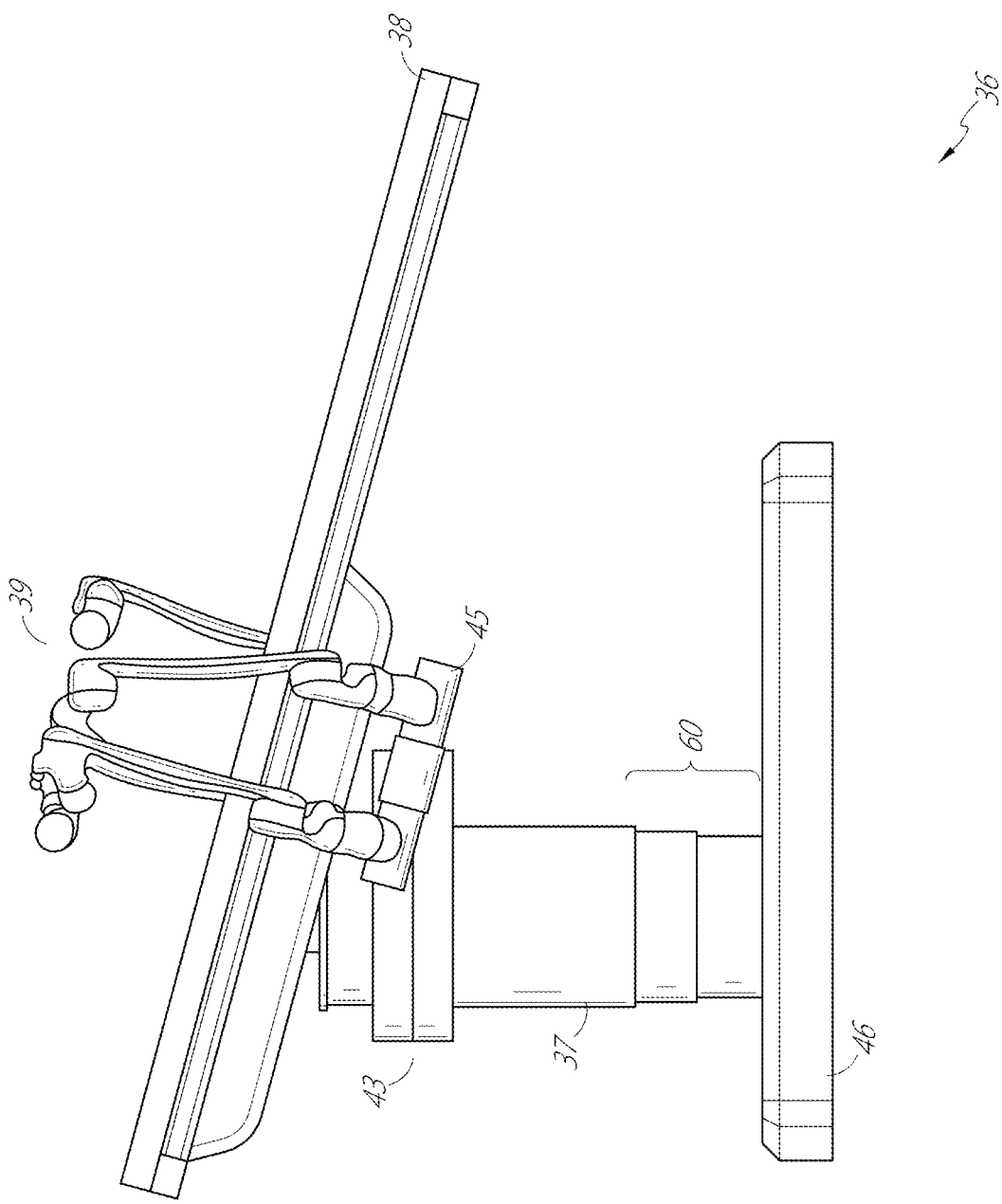
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
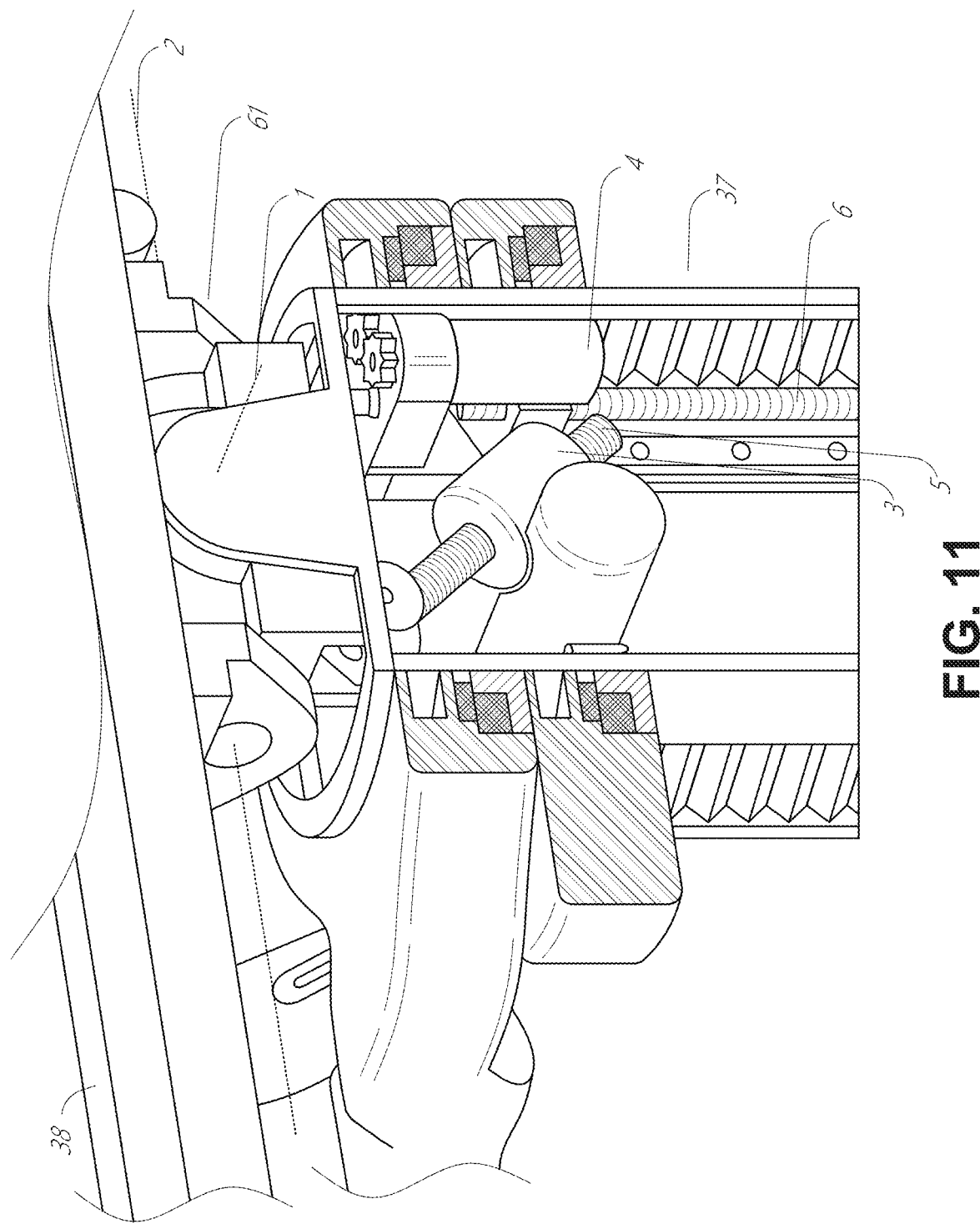
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
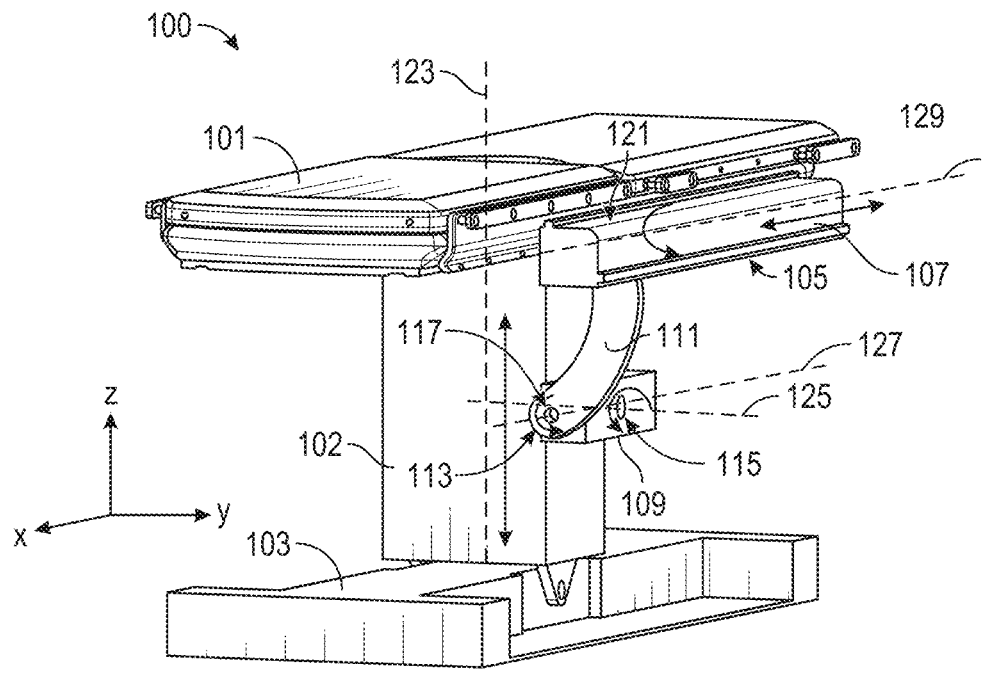
FIG. 12 illustrates an alternative embodiment of a table-based robotic system.
Figure 13:
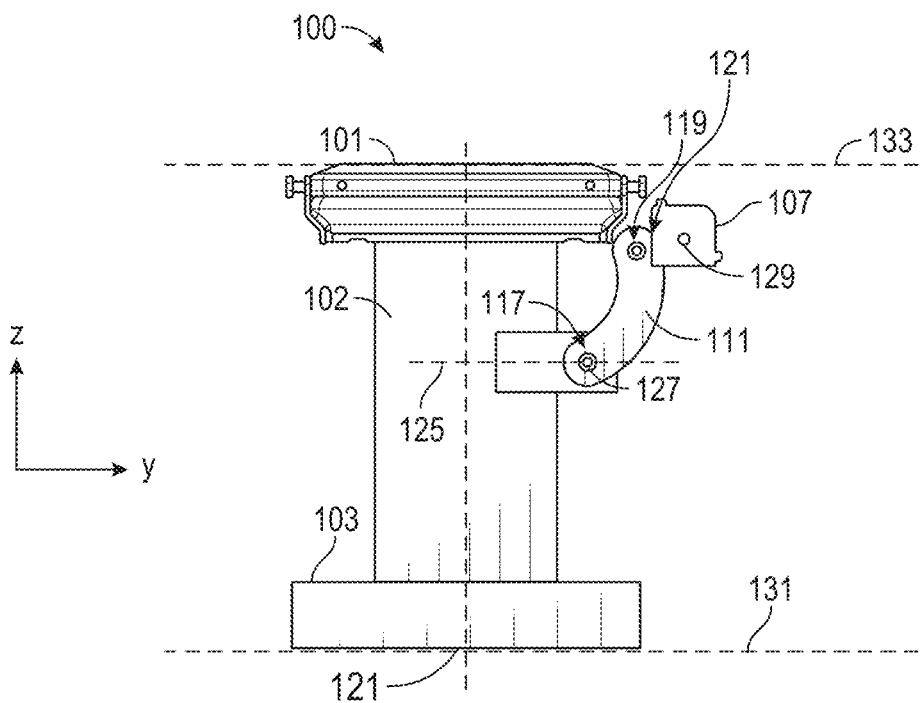
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
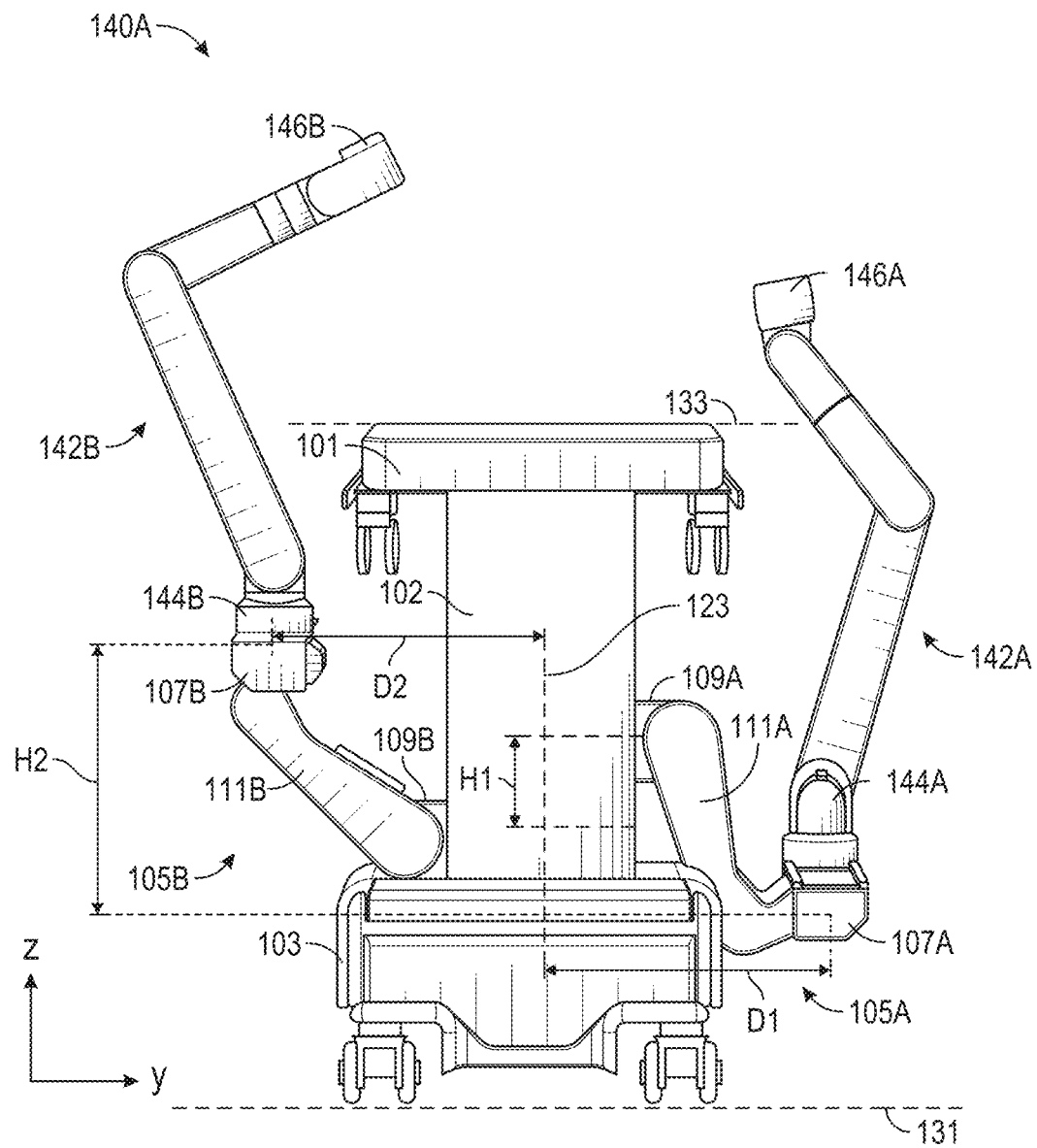
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
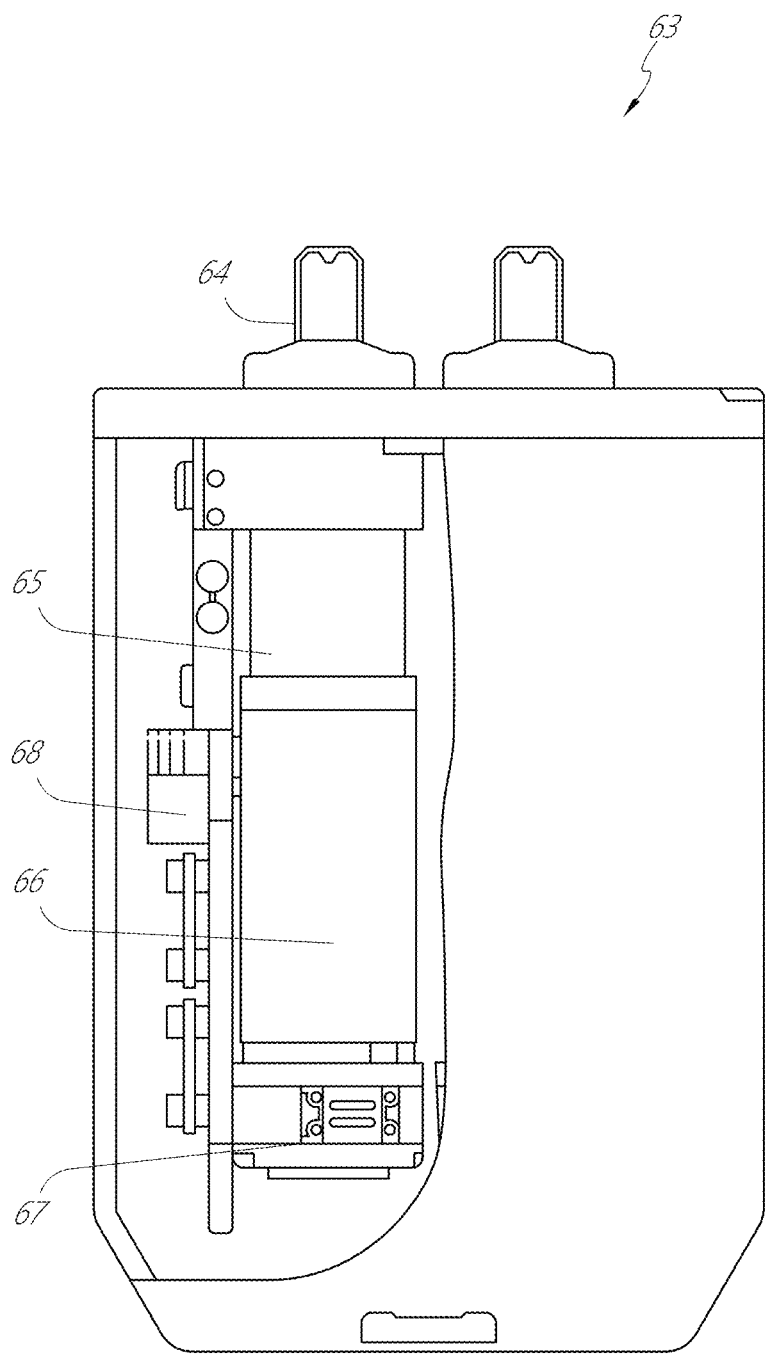
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
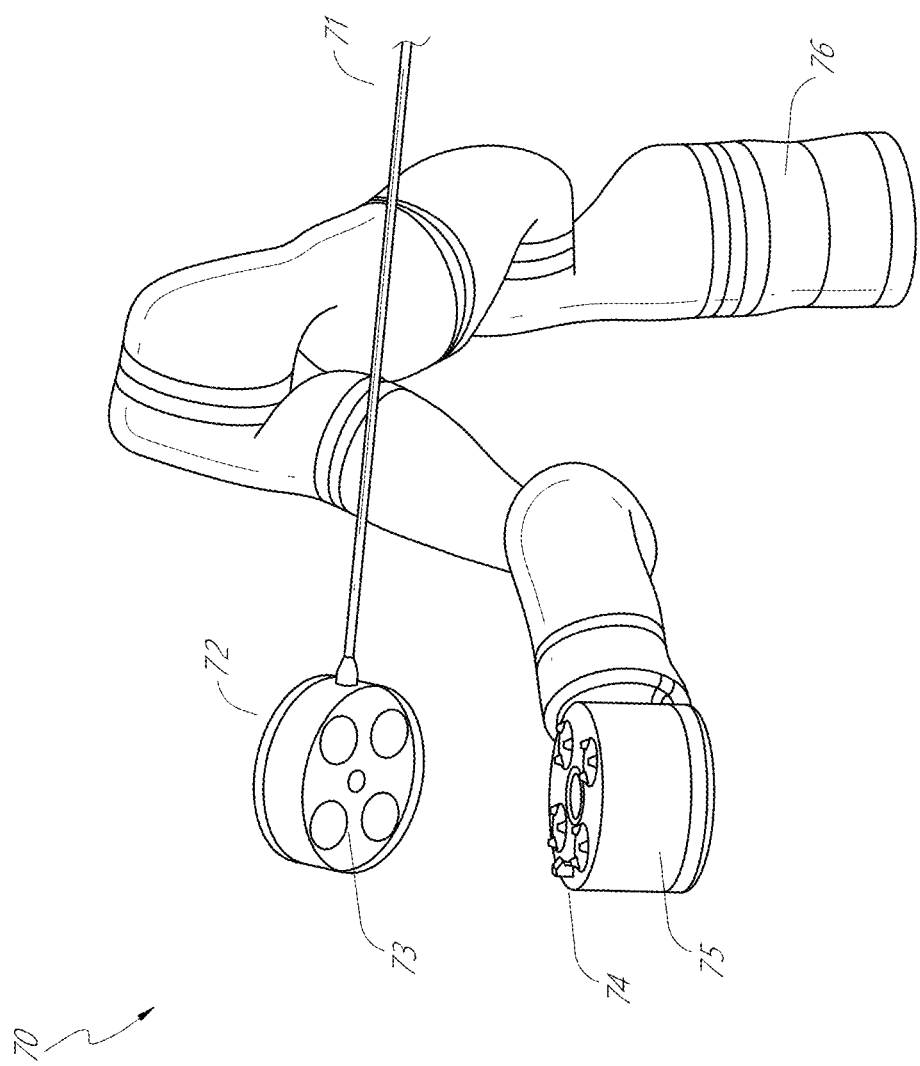
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bendable section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bendable section, torque exerted on drive inputs 73 would be transmitted down the tendons, causing the softer, bendable section (sometimes referred to as the articulable section or region) to bend or articulate. Along the non-bendable sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
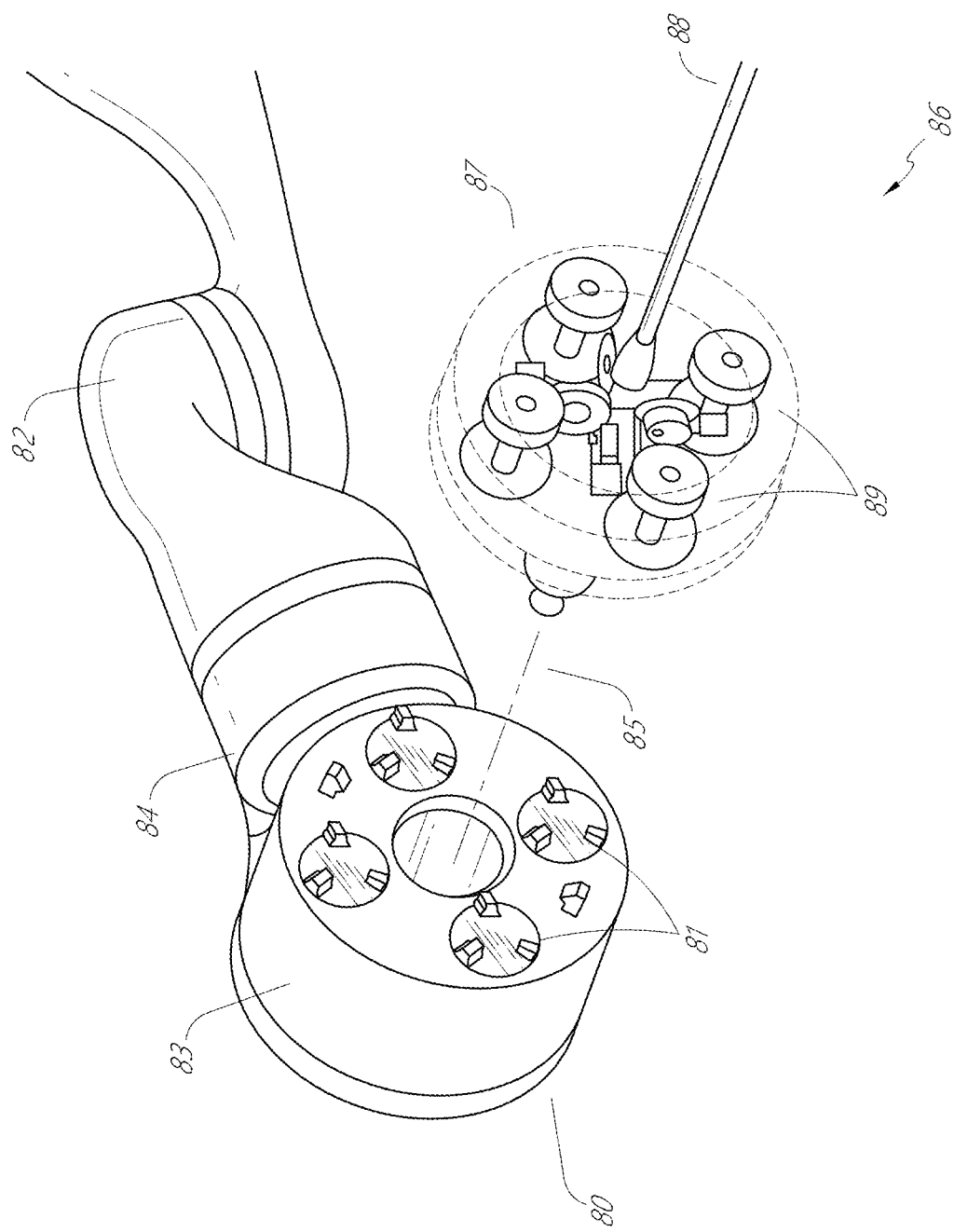
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
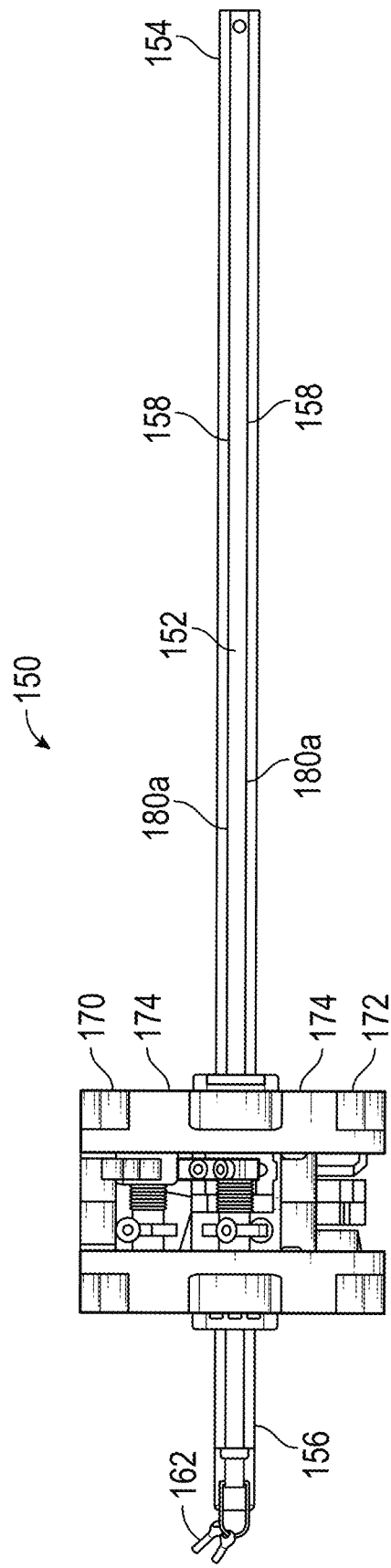
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
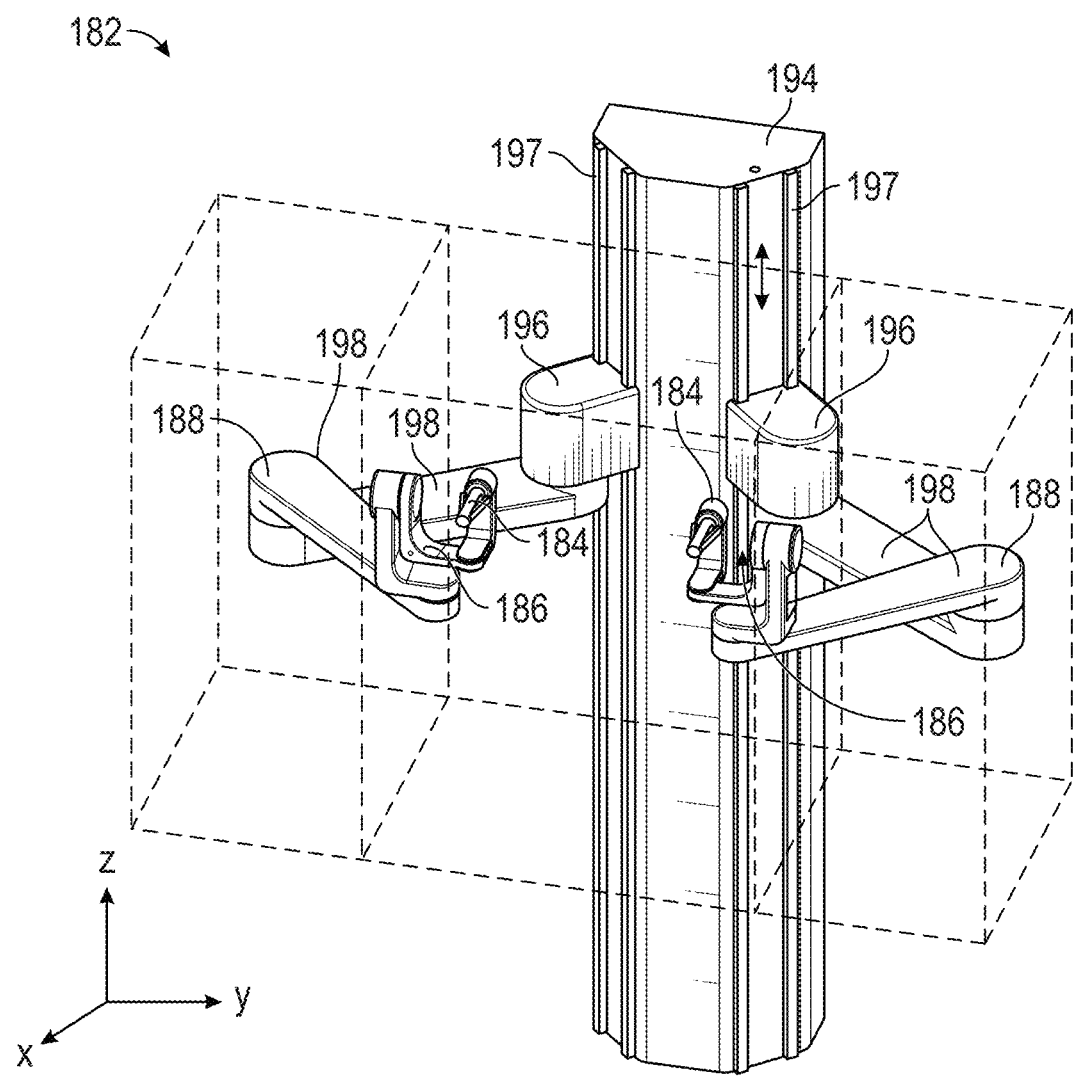
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
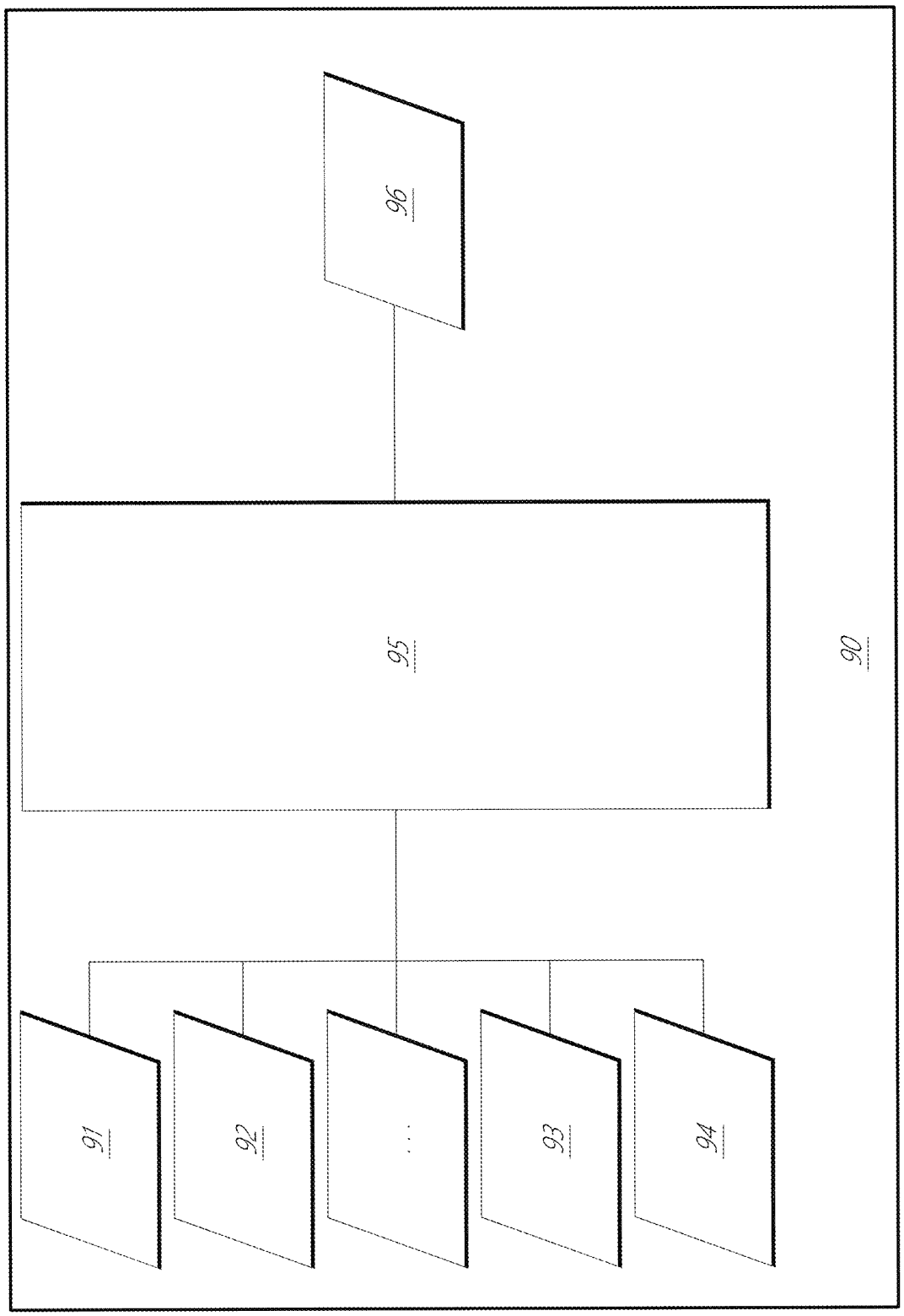
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety.

Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to a Medical Instrument with a Bendable section

Embodiments of the disclosure relate to systems and techniques related to a medical instrument that can include a bendable section articulable by cables.

Figure 21A:
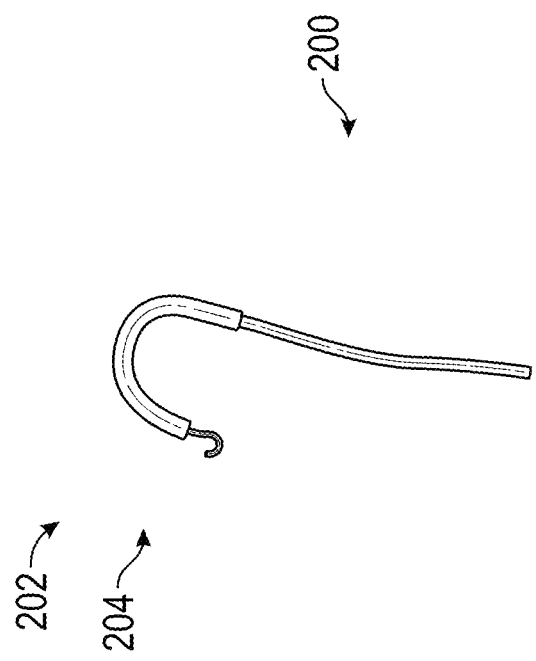
FIG. 21A illustrates an embodiment of a medical instrument with a series of articulable segments in a bent configuration.

FIG. 21A illustrates an example embodiment of medical instrument 200 that includes a bendable section 202 and a distal end 204. The bendable section 202 can couple to the distal end 204 such that bending of the bendable section 202 can articulate the distal end 204 of the medical instrument 200. The bendable section 202 is illustrated and described herein with respect to the illustrated medical instrument 200 which can be any of a variety of types of instruments including, but not limited to, endoscopes, gastroscopes, bronchoscopes, and/or ureteroscopes. The distal end 204 of the medical instrument 200 can include instruments and effectors such as, but not limited to, one or more forceps, guide wires, cutters, staplers, brushes, scopes, imaging devices, and the like and can include one or more passages for delivering such instruments and/or for delivering and/or removing fluids. While the bendable section 102 is described in the context of certain embodiments of medical instruments or robotic systems, the bendable section 102 can be used with other medical instruments and non-robotic systems.

Figure 21B:
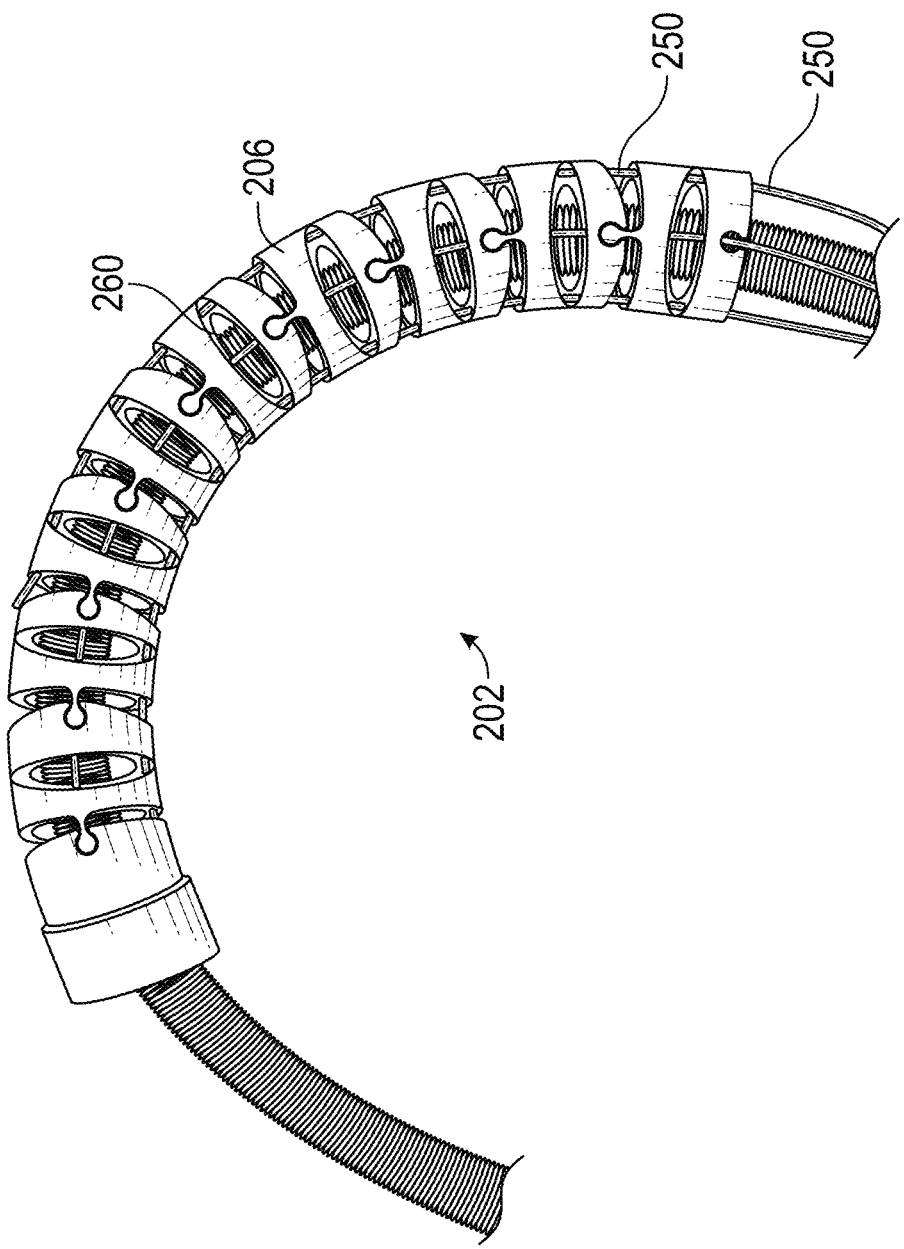
FIG. 21B illustrates an embodiment of a series of articulable segments.

FIG. 21B illustrates the bendable section 202 of the medical instrument 200 of FIG. 21A in additional detail. As shown, the bendable section 202 can be formed from a series of articulable segments 206. The bendable section 202 can have a length that defines an axis about which the bendable section 202 can bend. The series of articulable segments 206 can be operably coupled together to form the bendable section 202 such that articulation of the articulable segments 206 can cause the bendable section 202 to bend in at least one degree of movement. In some examples, the series of articulable segments 206 can allow the bendable section 202 to have at least two degrees of movement.

In some examples, the bendable section 202 of the medical instrument 200 can include one or more cables 250. The cables 250 and the articulable segments 206 of the bendable section 202 will be further described in paragraphs below.

Articulable Segments

Figure 25:
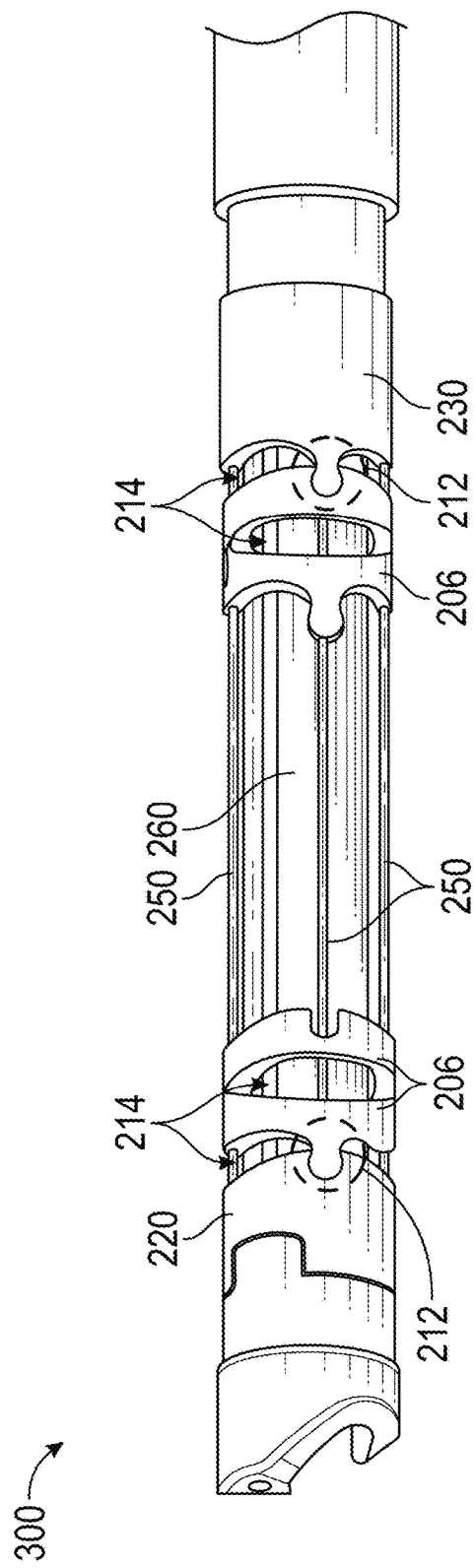
FIG. 25 illustrates an example embodiment of a medical instrument with a distal end segment, a proximal end segment, and articulable segments.

FIGS. 22A and 22B illustrate different views of the articulable segment 206 of FIG. 21B. The articulable segment 206 can include a body 216, one or more recesses 208, one or more protrusions 210, and one or more pathways 254. The body 216 can be ring-shaped and can include an opening 218 to allow an inner shaft 260 (e.g., as seen in FIG. 25) of the medical instrument 200 to extend through. The body 216 of the articulable segment 206 can be substantially circular in shape. In some examples, the opening 218 can be circular. The inner shaft 260 can be a tubular element through which other components can extend there through.

The one or more recesses 208 can be formed and/or coupled to a distal or a proximal side of the articulable segment 206. The one or more protrusions 210 can be formed and/or coupled to a distal or proximal side of the articulable segment 206. For example, the one or more recesses 208 can be formed on a distal side of the articulable segment 206 while the one or more protrusions 210 can be formed on a proximal side of the articulable segment 206. In another example, the one or more recesses 208 and the one or more protrusions 210 can be formed opposite sides of the articulable segment 206. Alternatively, the one or more recesses 208 and the one or more protrusions 210 can be positioned and/or formed on the same side of the articulable segments 206.

In some examples, each of the articulable segments 206 can include two recesses 208 and two protrusions 210, as shown in FIGS. 22A and 22B. The two recesses 208 can be formed on a first side of the articulable segment 206 while the two protrusions 210 can be formed on a second side of the articulable segment 206. The two recesses 208 can be positioned 180 degrees offset from each other. Similarly, the two protrusions 210 can be positioned 180 degrees offset from each other. The recesses 208 and the protrusions 210 can be positioned such that one of the recesses 208 (or one of the protrusions 210) is 90 degrees offset from the protrusions 210 (or the recesses 208).

The articulable segments 206 can couple to adjacent articulable segments 206 via their recesses 208 and the protrusions 210. For example, the recesses 208 of a first articulable segment 206 can couple to the protrusions 210 of a second articulable segment 206. In some examples, the second articulable segment 206 can be 90 degrees rotationally offset from the first articulable segment 206. Similarly, the recesses 208 of the second articulable segment 206 can couple to the protrusions 210 of a third articulable segment 206 that is 90 degrees rotationally offset from the second articulable segment 206.

In some examples, the bendable section 202 can include the series of articulable segments 206 where each subsequent articulable segment 206 can be offset by a predetermined angle from each preceding articulable segment 206. The predetermined offset angle can be between about 10 degrees and about 90 degrees, between about 20 degrees and about 80 degrees, between about 30 degrees and about 70 degrees, between about 40 degrees and about 60 degrees, or about 10 degrees, 20 degrees, 30 degrees, 40 degrees, 50 degrees, 60 degrees, 70 degrees, 80 degrees, 90 degrees, or ranges between any two of aforementioned values.

The pathways 254, as shown in FIGS. 22A and 22B, can be associated with the recesses 208 and the protrusions 210 of the articulable segment 206. The pathways 254 can extend through the width of the articulable segment 206, where the width corresponds to the thickness of the segment 206 in the longitudinal direction. The pathways 254 of the articulable segment 206 can allow the cables 250 (see FIG. 21B) to extend through the bendable section 202 of the medical instrument 200. In some examples, the pathways 254 can be enclosed openings as shown in FIGS. 22A and 22B. In other examples, the pathways 254 can be partially enclosed to form grooves.

FIG. 22C illustrates a series of articulable segments 206 which can be configured as described above with reference to FIGS. 22A and 22B connected in series. The recesses 208 and the protrusions 210 of the articulable segments 206 can be dimensioned to couple to form hinges 212. For example, the recesses 208 of a first articulable segment 206 can couple with the corresponding protrusions of a second articulable segment 206 that is immediately adjacent to the first articulable segment 206. Each pair of adjacent articulable segments 206 can include at least two hinges 212. As discussed above, the protrusions 210 and the recesses 208 can include the pathways 254 to allow the cable 250 (see FIG. 27A) to extend through. In this regard, each of the hinges 212 can include the pathway 254 to allow the cable 250 to extend through. In the example shown in FIG. 22C, the pathways 254 can be formed using a pair of perpendicular cuts or voids at each pathway 254 extending through the body. As seen in FIG. 22C, a cut on one side of the segment 206 can provide a recess 208 for a hinge, while a perpendicular cut on an opposite side of the segment 206 can extend through the protrusion 210 and intersect with the opposing cut to open up the pathway 254 extending through the hinge.

The recesses 208 and the protrusions 210 can be positioned such that the hinges 212 can be positioned between each of adjacent articulable segments 206. The hinges 212 can allow the articulable segments 206 to articulate (for example, rotate) about an axis that is transversal to the length of the bendable section 202. The hinges 212 that couple each pair of adjacent articulable segments 206, as discussed above, can allow the series of articulable segments to articulate the bendable section 202 to bend and/or articulate in one or more degrees of movement.

In some examples, each pair of adjacent articulable segments 206 can include a gap 214 formed between the articulable segments. The gap 214 can advantageously allow immediately adjacent articulable segments 206 to freely articulate without contacting each other and thereby limiting and/or reducing articulation angle of the bendable section 202.

Distal and Proximal End Segments

Figure 23B:
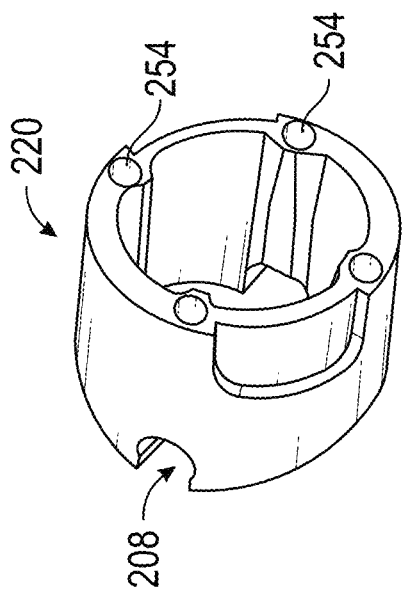
FIGS. 23A and 23B illustrate various views of an embodiment of a distal end segment.
Figure 23A:
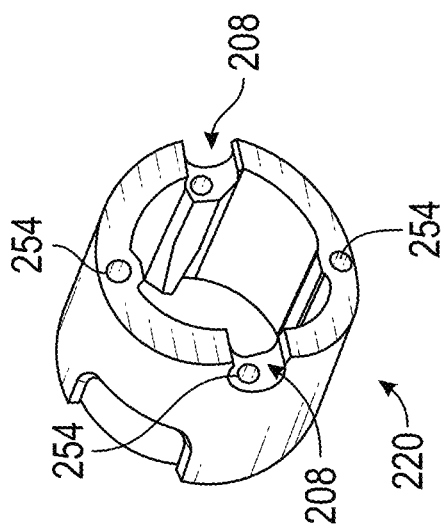

FIGS. 23A and 23B illustrate different views of an distal end segment 220 which can form part of or be otherwise coupled to the bendable section 202 described above. The distal end segment 220 can include one or more recesses 208 and/or one or more protrusions 210. The one or more recesses 208 or one or more protrusions 210 can be formed and/or positioned on a proximal side of the distal end segment 220. The distal end segment 220 can include one or more pathways 254. The pathways 254 can be associated with the recesses 208 and/or the protrusions 210. In some examples, the pathways 254 can be formed within the recesses 208 and/or the protrusions 210 such that the cable 250 can extend through the recesses 208 and/or the protrusions 210. The distal end segment 220 can include a cavity for the inner shaft 260 of the medical instrument 200.

Figure 24B:
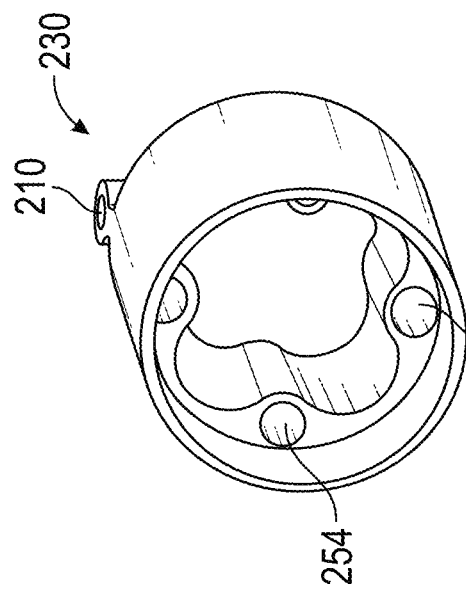
FIGS. 24A and 24B illustrate various views of an embodiment of a proximal end segment.
Figure 24A:
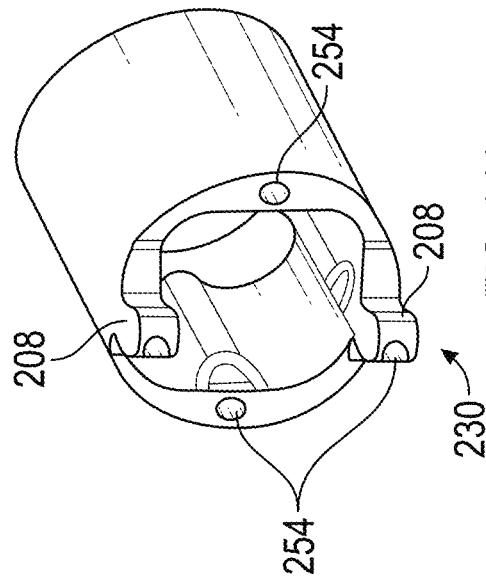

FIGS. 24A and 24B illustrate different views of an exemplary proximal end segment 230 that can in some embodiments form part of or be otherwise coupled to the bendable segment 202. The proximal end segment 230 can include one or more recesses 208 and/or one or more protrusions 210. The one or more recesses 208 or one or more protrusions 210 can be formed and/or positioned on a distal side of the proximal end segment 230. The one or more recesses 208 and/or one or more protrusions 210 can couple with one or more protrusions and/or one or more recesses of articulable segments 206. The proximal end segment 230 can include one or more pathways 254. The pathways 254 can be associated with the recesses 208 and/or the protrusions 210. In some examples, the pathways 254 can be formed within the recesses 208 and/or the protrusions 210 such that the cable 250 can extend through the recesses 208 and/or the protrusions 210. The proximal end segment 230 can include a cavity for the inner shaft 260 of the medical instrument 200.

In some examples, the proximal end segment 230 and the distal end segment 220 can have a cross-sectional area that is about the same as that of the articulable segments 206 of the bendable section 202. In other examples, the proximal end segment 230 and the distal end segment 220 can have a cross-sectional shape that is about the same or similar to that of the articulable segments 206. The distal end segment 220 and the proximal end segment 230 can provide ends to the bendable portion 202 and can be connected to other components of the medical device 200. In certain embodiments, the distal end segment 220 and/or the proximal end segment 230 can be omitted from the bendable portions 202 and/or portions of these segments can be combined with the distal or proximal most articulable segment.

FIG. 25 illustrates a distal portion of an exemplary medical instrument 300 that includes the distal end segment 220, the proximal end segment 230, and the articulating segments 206 as described above. In the illustration shown in FIG. 25, intermediate articulable segments 206 have been shown as being removed to better illustrate the cables 250.

As shown in FIG. 25, the one or more recesses 208 and/or one or more protrusions 210 of the distal end segment 220 and the proximal end segment 230 can couple with one or more protrusions and/or one or more recesses of articulable segments 206. As seen in FIG. 25, the protrusions and recesses form a series of hinges 212 in the bendable section 202 that connect the proximal end 230 segment, articulating segments 206, and distal end segment 220. The proximal end segment 230 and the distal end segment 220 can define a proximal end and a distal end of the bendable section 202. In some examples, the distal end segment 220 and the proximal end segment 230 can be fixedly attached to the medical instrument 300 such that the bendable section 202 can be fixedly attached to the medical instrument 300.

Support Sleeve

Figure 26A:
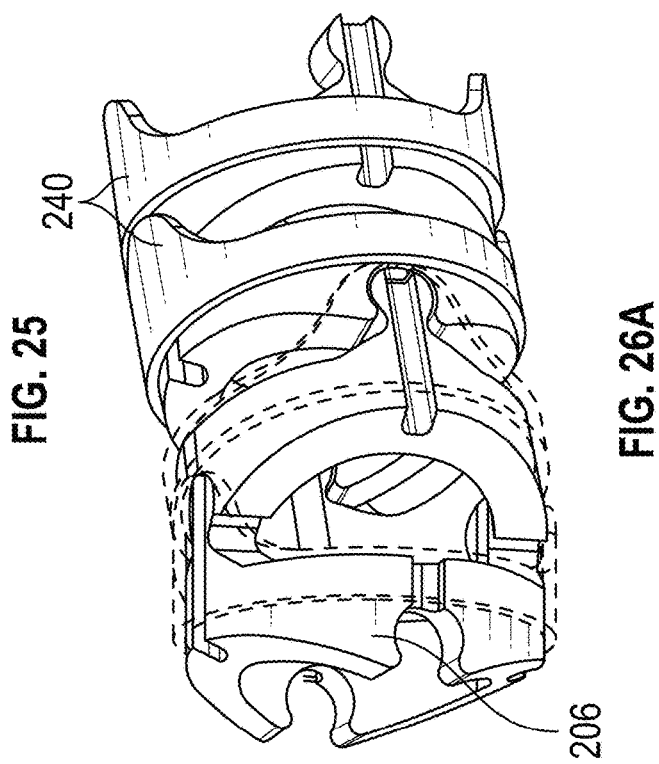
FIG. 26A illustrates an embodiment of a support member for an articulable segment.
Figure 26B:
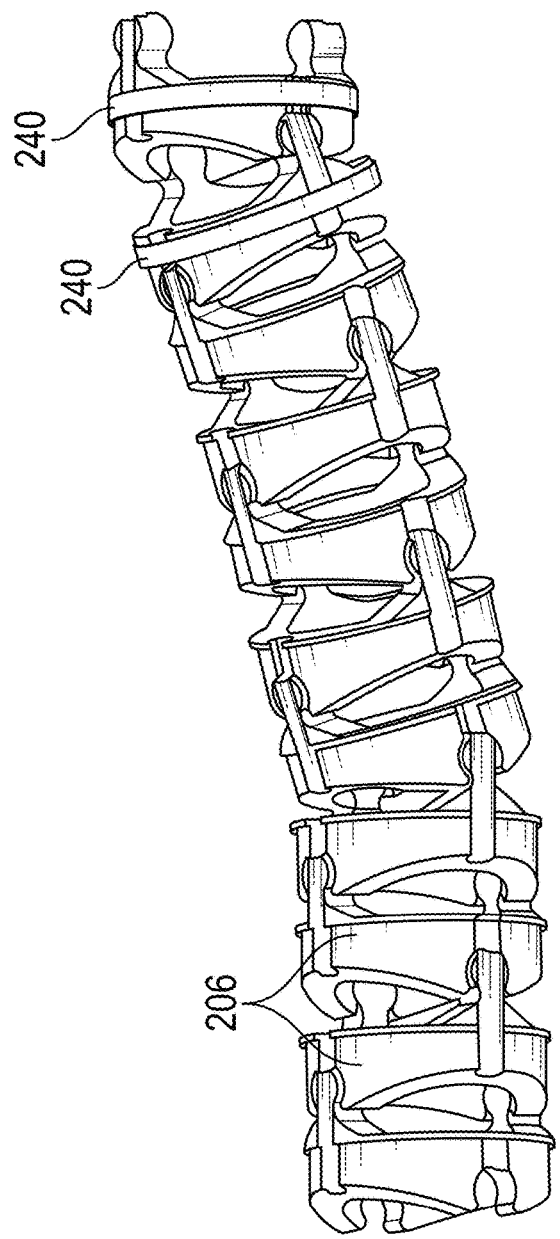
FIG. 26B illustrates another embodiment of a support member for an articulable segment.
Figure 26C:
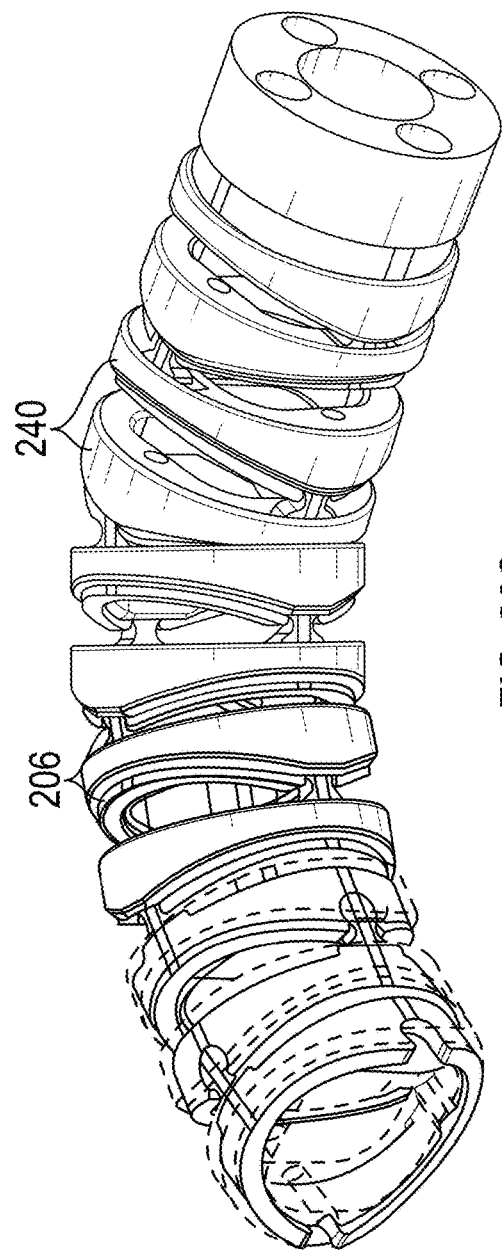
FIG. 26C illustrates another embodiment of a support member for an articulable segment.

FIGS. 26A-26C illustrate different exemplary support members 240 for a series of the articulable segments 206. The support members 240 can wrap at least a portion of the body 216 of the articulable segments 206. In some examples, the support members 240 can wrap individual articulable segments 206. The support members 240 and the articulable segments 206 can be made out of the same or different materials. Optionally, the support members 240 can couple to all articulable segments 206 of the medical instrument 200.

Pull Wire

Figure 27B:
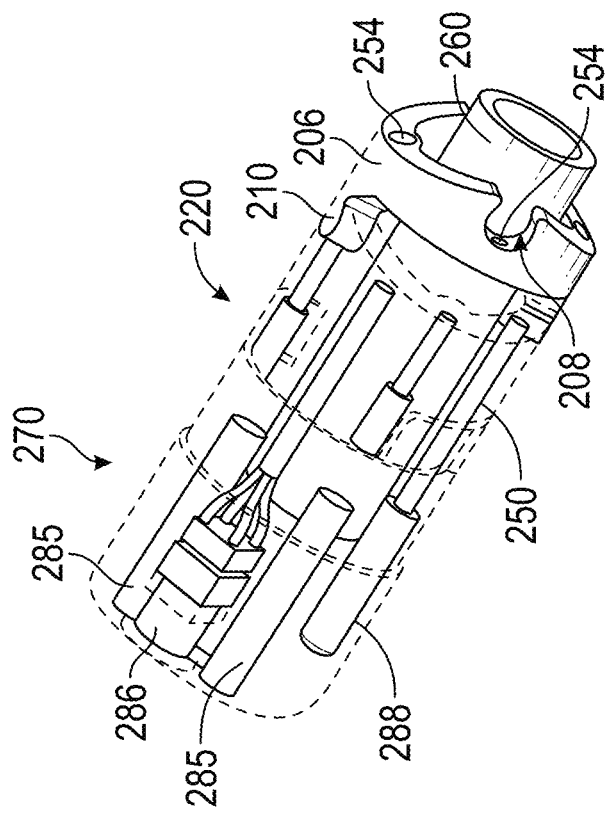
FIG. 27B illustrates an end portion of an medical instrument.
Figure 27A:
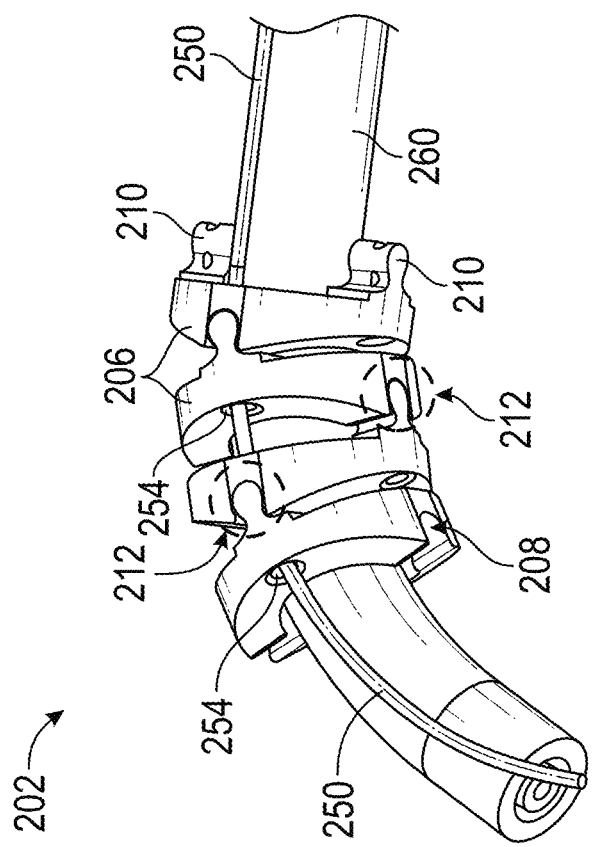
FIG. 27A illustrates a portion of a medical instrument with articulable segments and cables.

The medical instrument 200 can also include one or more cables 250. FIG. 27A illustrates the medical instrument 200 with a portion of the articulable segments 206 shown to illustrate the cables 250. The cables 250 can extend through the medical instrument 200 and can be used to articulate the medical instrument 200 in one or more degrees of movement (see FIGS. 28A and 28B). The cables 250 can be terminated at the distal end segment 220 as shown in FIG. 27B. The distal end segment 220 can be attached to a distal tip component 270 at a distal end or distal side of the distal end segment 220. The distal tip component 270 can provide a housing for holding one or more functional and/or electronic components. For example, one or more cameras 286, one or more illuminators 285, and/or one or more EM sensors 288 can be embedded in the distal tip component 270.

Pulling and/or relaxing a combination of the cables 250 can articulate the articulable segments 206 of the bendable section 202, causing the bendable section 202 to bend. When the cables 250 are pulled towards a proximal end of the medical instrument 200, they can engage the hinges 212 and the articulable segments 206 to cause them to actuate (e.g., rotate) about the axes associated with the hinges 212. In some examples, relaxing the cable 250 can cause the series of articulable segments 206 to articulate and bend the bendable section 202. In addition, the cables 250 can advantageously stabilize the bendable section 202 of the medical instrument 200, and provide biasing and predictability for operation of the medical instrument 200.

In some embodiments, the cables 250 may be under a predetermined tension. In this regard, increasing the amount of tension of one of the cables 250 while relaxing (e.g., reducing tension) an opposing cable 250 can articulate the articulable segments 206 and bend the bendable section 202.

Figure 28A:
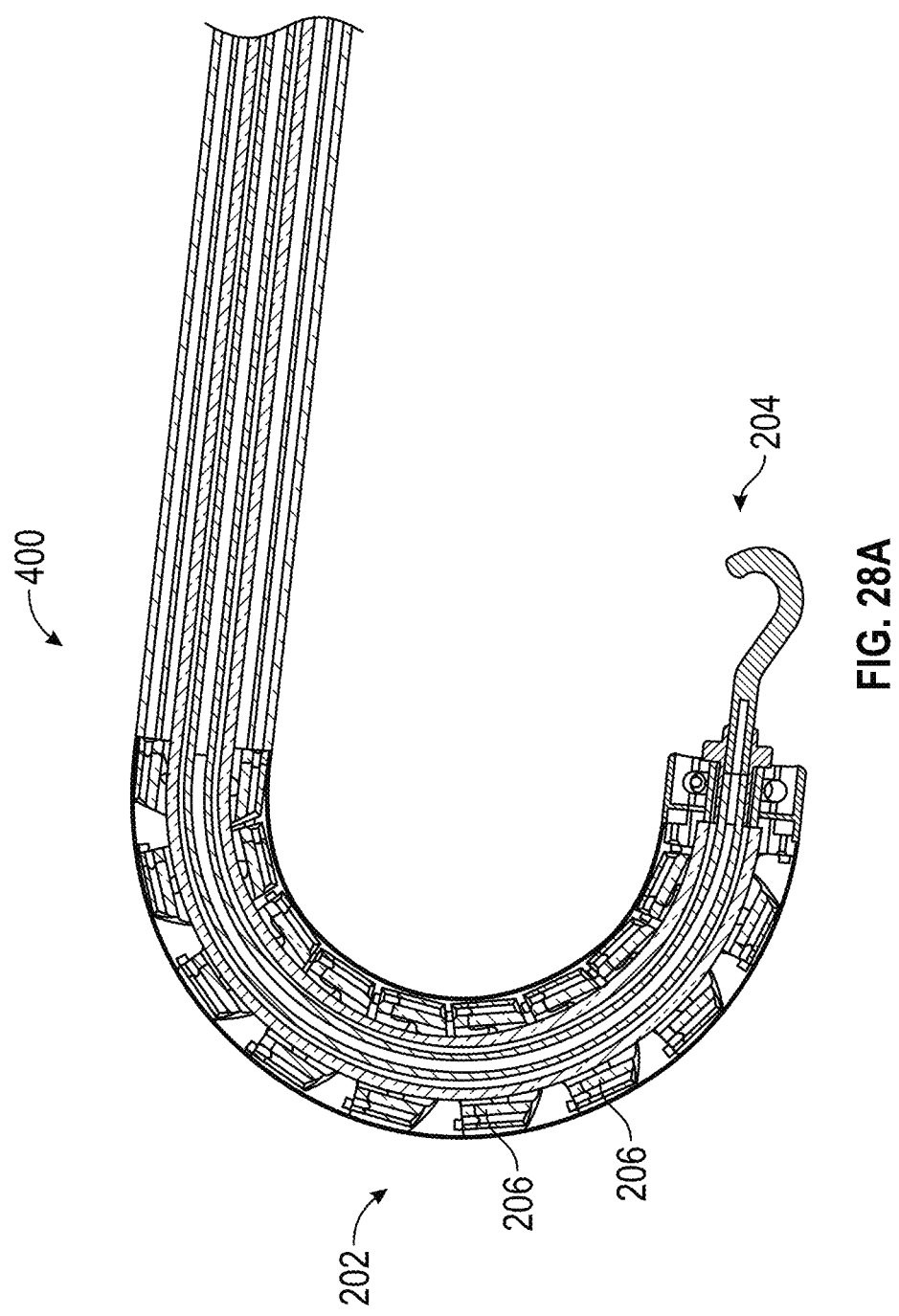
FIGS. 28A and 28B illustrate various views of an medical instrument in an articulated configuration.
Figure 28B:
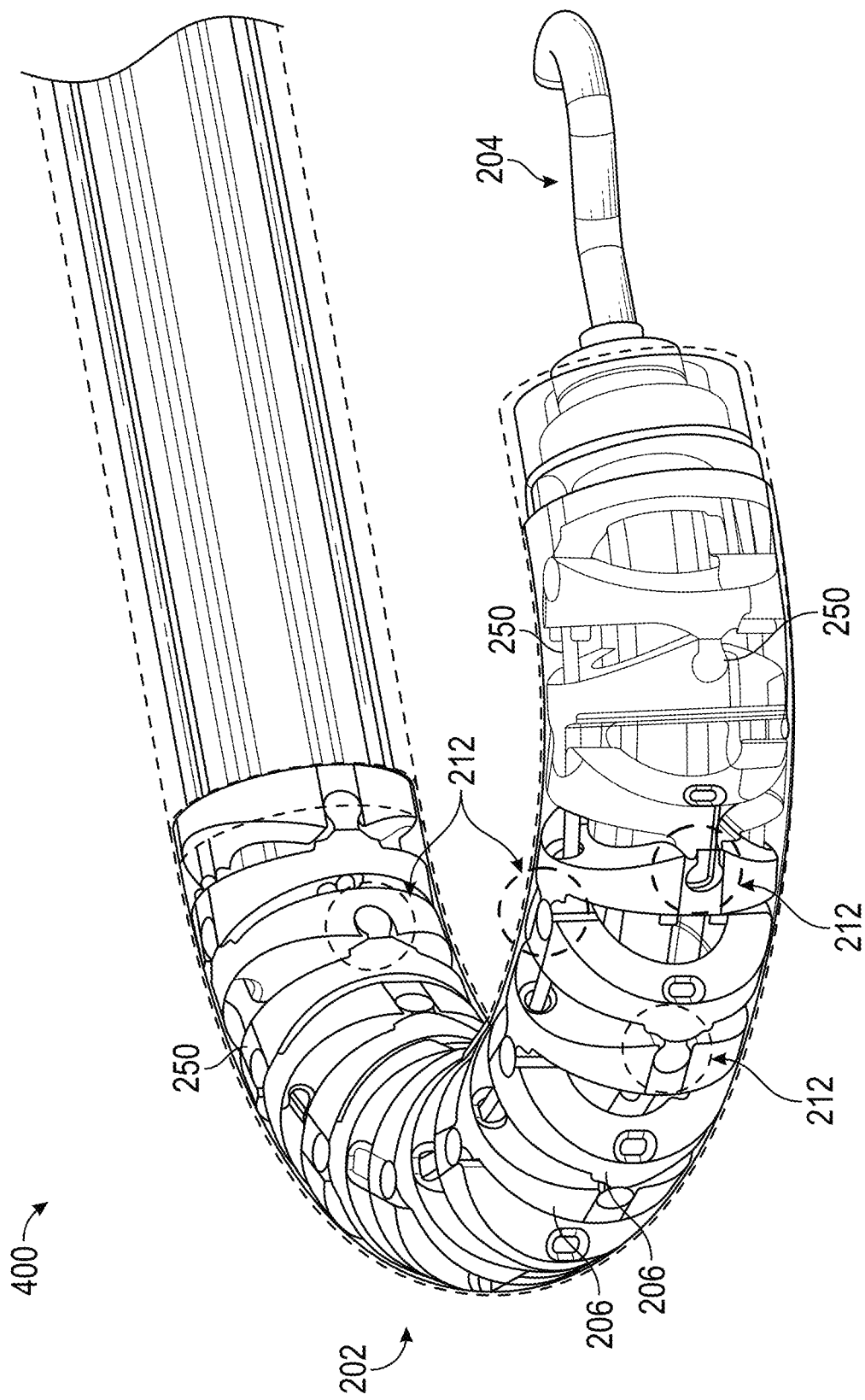

FIGS. 28A and 28B illustrates different views of the medical instrument 400 with the bendable section 202 bent. As discussed above, actuating (e.g., pulling/relaxing) one or more of the cables 250 can cause the bendable section 202 to bend. Actuating different combinations of the cables 250 can result in different orientations of the bendable section 202.

The cables 250 can be actuated using human interaction or robotic system including an actuator (or a controller). An actuator can be coupled to the cables 250 to pull/relax the cables 250. In some examples, separate actuators can be coupled to each of the cables 250 of the medical instrument 200. For example, the medical instrument 200 can include four cables 250 and four actuators coupled to the corresponding cables 250. In some embodiments, an actuator can be coupled to two or more of the cables and thus be configured to actuate multiple cables 250.

In some examples, simultaneous motion about two or more degrees of movement of the bendable section 202 can be accomplished by a more complex control scheme for pulling and/or pushing the cables 250. The control scheme can involve a computer-based control system that stores computer program instructions of a master device configured to interpret the motions of the user into corresponding actions of the medical instrument 200. The computer program may be configured to measure the electric load required to rotate the actuators (or input controllers) to compute the length and/or movement of the cables 250. The computer program may be further configured to compensate for changes in cable elasticity, such as if the cables 250 are a polymer, by increasing/decreasing the amount of rotation needed for the actuators (or input controllers) to change the length of the cable 250. The tension may be adjusted by increasing or decreasing the rotation of all the actuators (or input controllers) in coordination. The tension can be increased by simultaneously increasing rotation, and the tension can be decreased by simultaneously decreasing rotation. The computer program may be further configured to maintain a minimum level of tension in the cables 250. If the tension in any of the cables 250 is sensed to drop below a lower minimum tension threshold, then the computer program may increase rotation of all actuators (or input controllers) in coordination until the cable tension in all cables 250 is above the lower minimum tension threshold. If the tension in all of the cables 250 is sensed to rise above an upper minimum tension threshold, then the computer program may decrease rotation of all actuators (or input controllers) in coordination until the cable tension in any of the cables 250 is below the upper minimum tension threshold. The computer program may be further configured to recognize the grip strength of the operator based on the load of the motors actuating the actuators (or input controllers) coupled to the cables 250.

Tip Assembly

Figure 29A:
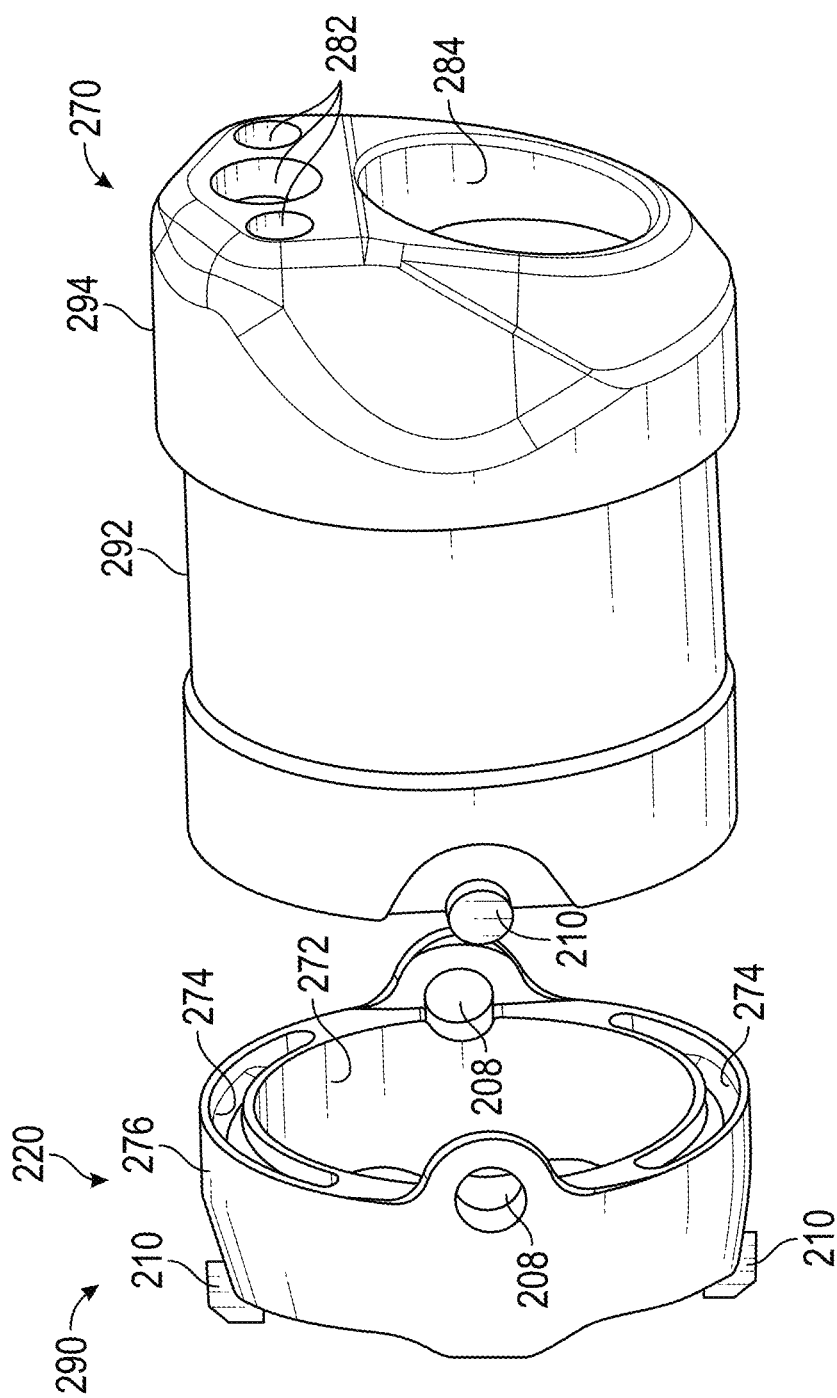

The medical instrument 200 can include a tip assembly 290 that facilitates attachment of the one or more cables 250 and/or embedding or housing of one or more functional and/or electronic components in the distal tip of the instrument. FIGS. 29A-29B illustrate examples of a tip assembly 290 that can be used at a distal tip of the medical instrument 200, for example at the distal end of the elongated shaft 71 (FIG. 16). FIG. 29A shows the tip assembly 290 in an unassembled configuration, while FIG. 29B shows the tip assembly 290 in an assembled configuration in which it is attached at the distal end of the bendable section 202.

The tip assembly 290 includes distal end segment 220 and a distal tip component 270. The distal end segment 220 can be configured as a control member to which one or more cables 250 are anchored. Accordingly, the distal end segment 220 can provide a termination and fixation point for cables 250, which can be configured to bend the bendable section and thereby steer the tip assembly 290 based on forces applied to the cables 250. The distal tip component 270 provides a housing that serves to hold functional components therein. For example, one or more electronic components, such as one or more cameras, one or more LEDs, one or more optical fibers, and/or one or more EM sensors can be embedded in the distal tip component 270 to provide functionality associated with a scope or other type of medical instrument.

As seen in FIGS. 29A-29B, the distal tip component 270 can be a separate part from the distal end segment 220. By providing the distal end segment 220 and the distal tip component 270 as a separate parts attached to each other, manufacturing or design constraints can be removed. For example, the cables 250 can be attached and anchored to the distal end segment 220 by soldering the cables thereto, while electronic components can be embedded in the distal tip component in a separate operation. The housing which holds electronic components can thus, for example, be freed of a constraint requiring soldering of the cables 250 thereto, allowing the housing to be made shorter or be more easily machined with complex geometries. Additionally or alternatively, such a construction can allow portions of the bendable section and the distal tip component to have different useful lives and be readily separable for sterilization or re-use of one component or the other. As an example, this may allow the distal tip component 270 to be separated from the bendable section, so that the bendable section may be discarded while distal dip component 270 and functional components therein, such as imaging devices, position sensors, and/or other electronic components, may be re-used for a longer useful life. [0146] The distal end segment 220 can be configured as a control ring or ring-shaped segment having an annular portion 276 and a central opening 272 extending through the annular portion 276. The distal end segment 220 can include one or more slots 274 formed therein. The slots 274 can be formed in the annular portion 276 and can provide a fixation point for anchoring the cables 250 thereto. For example, the cables 250 can be bonded to the slots 274 by soldering the cables 250 to the annular portion 276 in the slots 274 so as to form a strong and secure attachment that allows the scope to be reused for multiple procedures. Alternatively, or in combination, the cables 250 can be anchored to the distal end segment 220 via adhesive, welding, or any suitable attachment technique.

The distal end segment 220 can include recesses 208 and/or protrusions 210 to facilitate hinged connection and/or snap-fit connection to other segments that are on or otherwise coupled to the elongate shaft 72. In the example shown, a proximal side of the distal end segment 220 includes protrusions 210 that are configured to connect to an adjacent articulating segment 206 of the bendable section 202. Accordingly, forces applied to the distal end segment 220, via the control cables 250, can transmit to components of the tip assembly 290 that are fixed to the distal end segment 220, and such forces can bend the bendable section 206 to steer the tip assembly 290 in a desired direction. The slots 274 can be circumferentially and axially aligned with the hinges on a proximal side of the ring, which are joined to a proximal articulating segment, to facilitate routing of the cables 250 through the hinges and to the anchoring point in the slots 274.

The distal side of the distal end segment 220 is also shown with recesses 208, which are configured to connect to protrusions 210 on a proximal side of the distal tip component 270. The protrusion connection to the distal tip component 270 can facilitate manufacturing by, for example, allowing a snap fit to mechanically connect the distal end segment 220 to the distal tip component 270. It may be desirable to rigidly attach the distal end segment 220 to the distal tip component 270 so that there is no relative motion or rotation therebetween. This can permit the distal end segment 220 to act as a control member that steers the functional components within the distal tip component 270 directly in a precise manner where the motion of the control member substantially matches the motion of the functional components. The hinge coupling can be converted to a rigid connection by, for example, having the distal side of the distal end segment 220 and the proximal side of the distal tip component 270 adjoin substantially flush with each other. The distal side of the distal tip component 270 substantially flush with the proximal side of the distal tip component 270 can restrict relative rotation between the control member and the distal tip component 270 about the hinge coupling. Additionally or alternatively, such a rigid connection can be achieved by inserting a component, such as a potting adhesive, into the space near the interface between the distal end segment 220 and distal tip component 270 to fix such parts together. Additionally or alternatively, such a compound can serve to provide a seal between such parts and/or seal functional components within the distal tip component 270.

The recesses 208 and protrusions 210 forming the hinge connections can take a variety of shapes, sizes, and/or orientations in various embodiments. In FIGS. 29A-29B, the protrusions 210 are configured as radial protrusions that extend outward in a radial direction. In various embodiments, the protrusions can, for example, extend radially inward, radially outward, longitudinally in a proximal direction, or longitudinally in a distal direction.

The distal tip component 270 can be provided with one or more openings for fitting functional components therein and/or for permitting other instruments to be inserted therethrough. For example, the distal tip component 270 can include one or more ports 282 and an opening of a working channel 284. The one or more ports 282 can be configured to hold optical devices, such as cameras 286 and/or illuminators 285, configured to facilitate visualization of an internal anatomy of a patient. It is contemplated that any appropriate number of one or more ports 282 may be used for holding one or more functional components. In the example shown in FIG. 29A, three ports 282 are shown. The middle of the three ports can hold a camera 286 therein, which can have a field of view extending distally out of the port. Each of the other two ports can hold an illuminator 285 therein, such as an LED or optical fiber, which can provide illumination distally to illuminate at least a portion of the field of view of the camera. The opening of the working channel 284 can allow other instruments, such as biopsy needles, graspers, and/or treatment delivery devices to be inserted therethrough. Such other instruments may be configured to pass through the central opening 272 of the distal end segment 220, the opening of the working channel 284 in the distal tip component 270, and out of the distal end of the tip assembly 290 when inserted therethrough. In some embodiments, the distal end segment 220 can enclose a proximal part of one or more of the electronic and/or functional components embedded within the distal tip component 270. For example, the EM sensor 288 may have a length such that a proximal end of the EM sensor 288 protrudes proximally out of the proximal side of the distal tip component 270 when the distal end segment 220 is manufactured as a separate part. However, the distal end segment 220 can be configured to surround the proximal end of the EM sensor 288 to provide a seal around such component.

The distal tip component 270 can include a proximal section 292 and a distal section 294. The proximal section 292 can have a reduced outer diameter relative to the distal section 294, such that the distal section 294 is provided with a flange portion that protrudes radially relative to the outer diameter of proximal section 292. The distal end segment 220 can also have a reduced outer diameter relative to the distal section 294, for example, by having an outer diameter that substantially matches the outer diameter of the proximal section 292. The reduced outer diameter of proximal section 292 can allow for a sleeve (or "jacket") to extend around the outer surface of the proximal section 292 (or otherwise be fitted over the control member), adjoin the distal section 294 (e.g., abut against the proximal side of the flange portion), and form a lap joint with the distal section 294 for secure attachment. Such a sleeve (not visible in FIGS. 29A-29B) can also extend around the distal end segment 220 and articulating segments 206, to thereby enclose and/or seal components therein.

In the illustrated example, the distal end segment 220 providing the control member and the distal tip component 270 providing the housing are axially arranged, with the housing disposed distal to the control member so as to hold functional components at a leading terminal end of the instrument. Such an arrangement can improve manufacturability or steerability of the instrument. However, it is also contemplated that the control member for anchoring the cables 250 and the housing for holding embedded components can be arranged laterally with respect to each other.

3. Implementing Systems and Terminology.

Implementations disclosed herein provide systems and apparatus for an medical instrument including a bendable section articulable by cables.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions of pulling and/or relaxing of the cables described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical instrument comprising:
   an elongate body having a distal end and a proximal end;
   a bendable section positioned proximal to the distal end having at least two degrees of movement, the bendable section comprising a series of articulable segments positioned along the bendable section, wherein:
   the series of articulable segments includes at least one pair of adjacent articulable segments comprising a first articulable segment and a second articulable segment,
   the first and second articulable segments are connected by a first hinge and a second hinge,
   the first hinge is formed by a first protrusion of the first articulable segment and a corresponding first recess of the second articulable segment,
   the second hinge is formed by a second protrusion of the first articulable segment and a corresponding second recess of the second articulable segment,
   the first recess is formed on a first axial side of the second articulable segment, and
   a first perpendicular cut is formed on a second axial side of the second articulable segment that extends through a body of the second articulable segment to intersect with the first recess to form a cable pathway through the second articulable segment; and
   at least one cable extending through the cable pathway.

2. The medical instrument of claim 1, wherein a second perpendicular cut is formed through the first protrusion on a side of the first articulable segment that faces the first axial side of the second articulable segment.

3. The medical instrument of claim 1, further comprising a third articulable segment connected to the second articulable segment, wherein the second and third articulable segments are connected by third and fourth hinges that are positioned 90 degrees offset from the first and second hinges, wherein the third and fourth hinges are each formed by a recess or protrusion of the second articulable segment that engages a corresponding recess or protrusion of the third articulable segment.

4. The medical instrument of claim 1, wherein the first perpendicular cut is laterally open on first and second ends thereof.

5. The medical instrument of claim 1, wherein the the second axial side of the second articulable segment comprises third and fourth protrusions that alternate around a circumference of the second articulable segment with the first and second recesses, the first and second recesses being formed on the first axial side of the second articulable segment.

6. The medical instrument of claim 5, wherein third and fourth recesses are formed on the first side of the second articulable segment opposite the third and fourth protrusions, respectively.

7. The medical instrument of claim 5 further comprising:
   a second perpendicular cut formed on the second axial side of the second articulable segment opposite the second recess;
   a third perpendicular cut formed on the second axial side of the second articulable segment through the third protrusion; and
   a fourth perpendicular cut formed on the second axial side of the second articulable segment through the fourth protrusion;
   wherein:
   the first and second perpendicular cuts are parallel to one another; and
   the third and fourth perpendicular cuts are parallel to one another and perpendicular to the first and second perpendicular cuts.

\* \* \* \* \*